(12) United States Patent
Kim

(10) Patent No.: US 11,253,698 B2
(45) Date of Patent: Feb. 22, 2022

(54) METHOD FOR POSITIONING TERMINAL END OF PACEMAKER LEAD, WHICH HAS PASSED THROUGH CORONARY SINUS, IN INTERVENTRICULAR SEPTUM

(71) Applicant: TAU PNU MEDICAL CO., LTD., Busan (KR)

(72) Inventor: June-hong Kim, Busan (KR)

( * ) Notice: Subject to any disclaimer, the term of this patent is extended or adjusted under 35 U.S.C. 154(b) by 188 days.

(21) Appl. No.: 16/409,764

(22) Filed: May 10, 2019

(65) Prior Publication Data

US 2020/0046965 A1 Feb. 13, 2020

Related U.S. Application Data

(63) Continuation of application No. 15/328,046, filed as application No. PCT/KR2015/006044 on Jun. 16, 2015, now Pat. No. 10,335,589.

(30) Foreign Application Priority Data

Jul. 22, 2014 (KR) .................. 10-2014-0092789

(51) Int. Cl.
*A61N 1/05* (2006.01)
*A61B 17/34* (2006.01)
(Continued)

(52) U.S. Cl.
CPC .............. *A61N 1/056* (2013.01); *A61B 17/34* (2013.01); *A61B 17/3468* (2013.01); *A61B 17/3478* (2013.01); *A61M 25/003* (2013.01); *A61M 25/0071* (2013.01); *A61M 25/0074* (2013.01); *A61M 25/0082* (2013.01);
(Continued)

(58) Field of Classification Search
CPC .............. A61N 1/0587–0597; A61N 1/056–2001/0585; A61F 2/2427–2439; A61F 2/2466; A61F 2002/2484; A61B 17/3403–2017/3413
See application file for complete search history.

(56) References Cited

U.S. PATENT DOCUMENTS

2006/0106442 A1* 5/2006 Richardson .......... A61N 1/0587 607/119
2008/0242976 A1* 10/2008 Robertson .......... A61N 1/36514 600/425

(Continued)

*Primary Examiner* — Darwin P Erezo
*Assistant Examiner* — Brigid K Byrd

(57) ABSTRACT

The present invention relates to a method for positioning a tip of a pacemaker lead that has passed through coronary sinus into an interventricular septum. More particularly, it relates to a method for positioning a tip of a pacemaker lead that has passed through a coronary sinus into an interventricular septum in order to more effectively transmit an electrical stimulus in a treatment using a pacemaker for patients with arrhythmia.

A method of positioning a tip of a pacemaker lead, which has passed through a coronary sinus, into an interventricular septum, in order to effectively transmit electrical stimulus, includes: inserting into an intervention wire through a superior vena cava and a coronary sinus to pass through the interventricular septum and then guiding the intervention wire to an inferior vena cava; and positioning the tip of the lead into the interventricular septum by inserting the pacemaker lead along the intervention wire.

24 Claims, 21 Drawing Sheets

(51) Int. Cl.
    *A61M 25/10*      (2013.01)
    *A61M 25/00*      (2006.01)
    *A61M 25/04*      (2006.01)
    *A61M 25/01*      (2006.01)
    *A61B 17/00*         (2006.01)
    *A61B 17/22*         (2006.01)

(52) U.S. Cl.
    CPC ........ *A61M 25/0194* (2013.01); *A61M 25/04* (2013.01); *A61M 25/10* (2013.01); *A61N 1/05* (2013.01); *A61B 2017/00247* (2013.01); *A61B 2017/00252* (2013.01); *A61B 2017/22044* (2013.01); *A61B 2017/3405* (2013.01); *A61M 25/007* (2013.01); *A61M 25/0041* (2013.01); *A61M 25/0108* (2013.01); *A61M 2025/0079* (2013.01); *A61M 2025/0096* (2013.01); *A61M 2025/1052* (2013.01); *A61M 2025/1079* (2013.01); *A61M 2025/1093* (2013.01); *A61N 1/0565* (2013.01)

(56) References Cited

U.S. PATENT DOCUMENTS

2011/0098720 A1\* 4/2011 Taylor ................ A61B 17/3468
                                                        606/129
2011/0313434 A1\* 12/2011 Kocaturk ............. F16G 11/101
                                                        606/148

\* cited by examiner

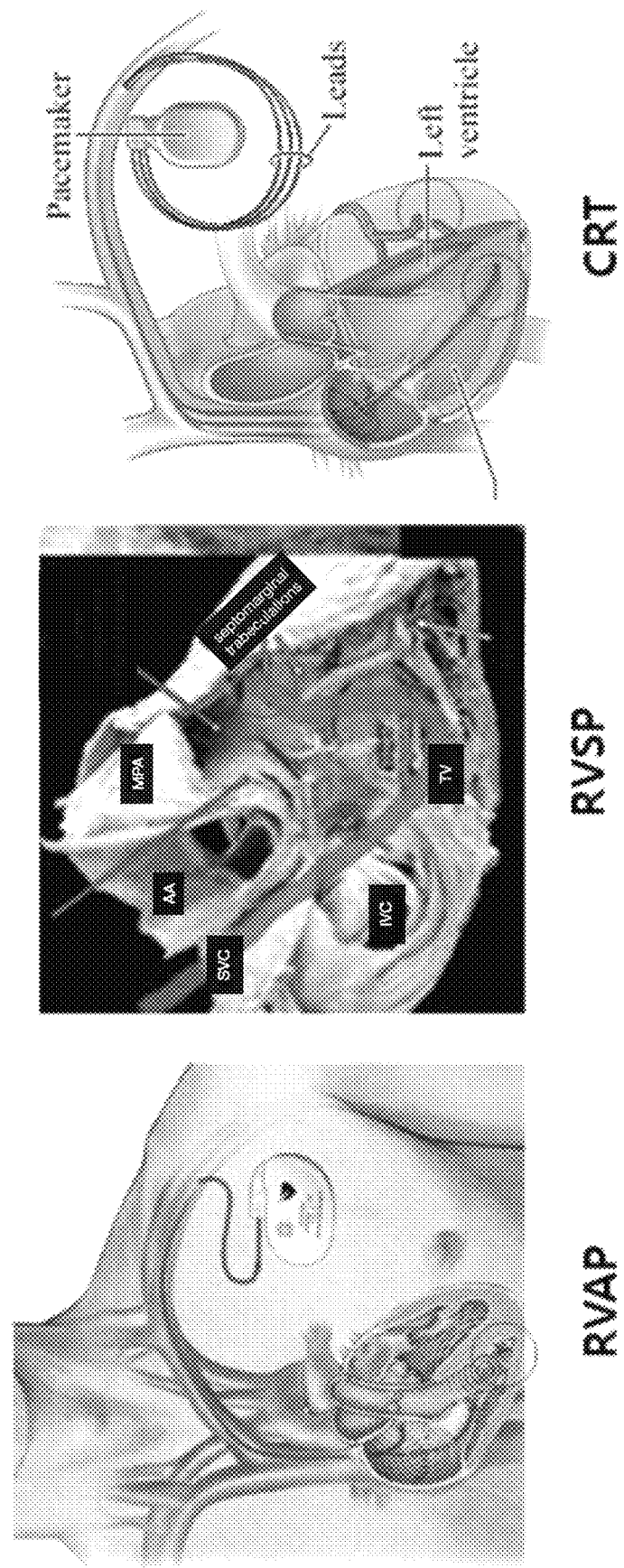

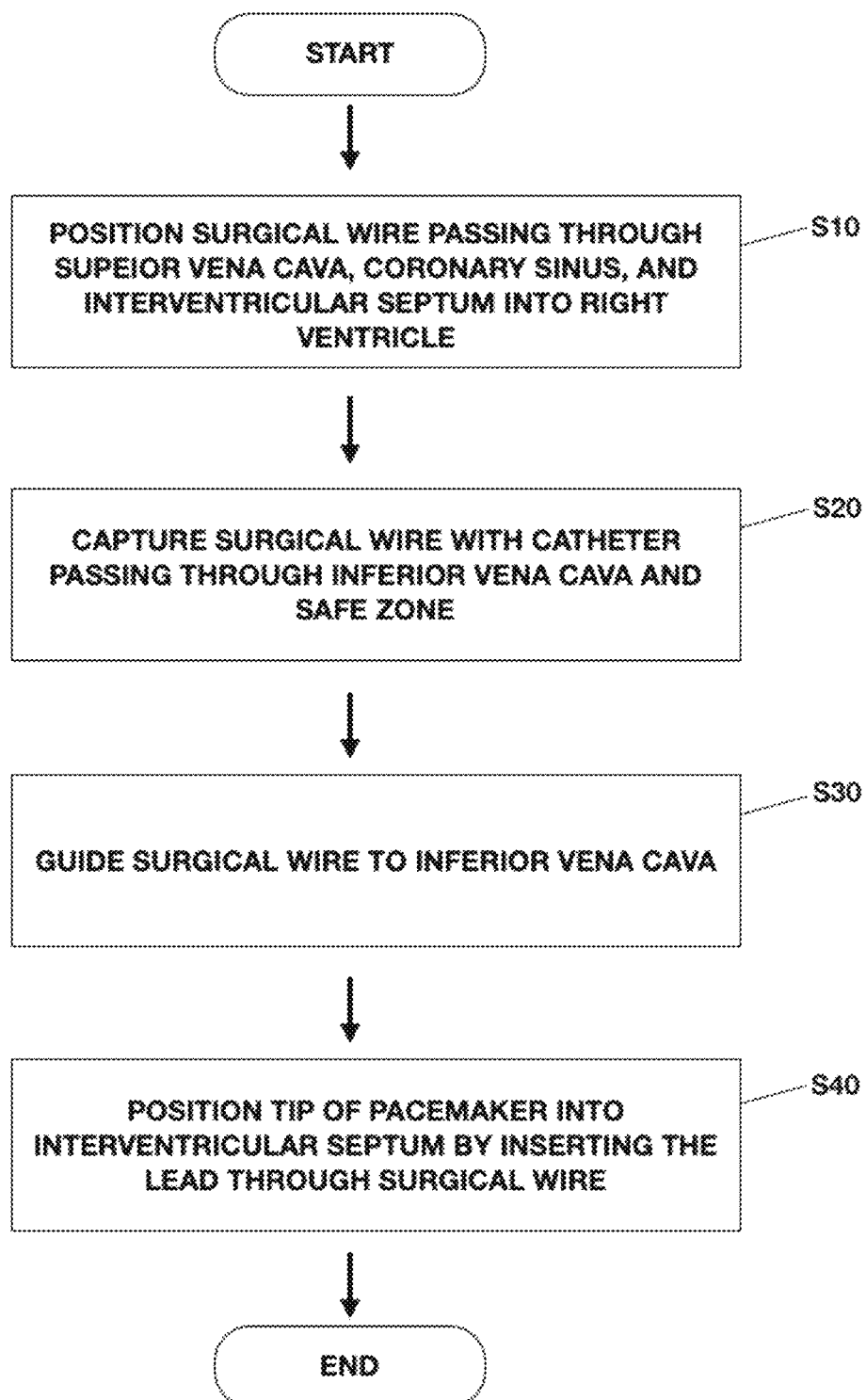

Pressurized septal venogram

FIG. 6
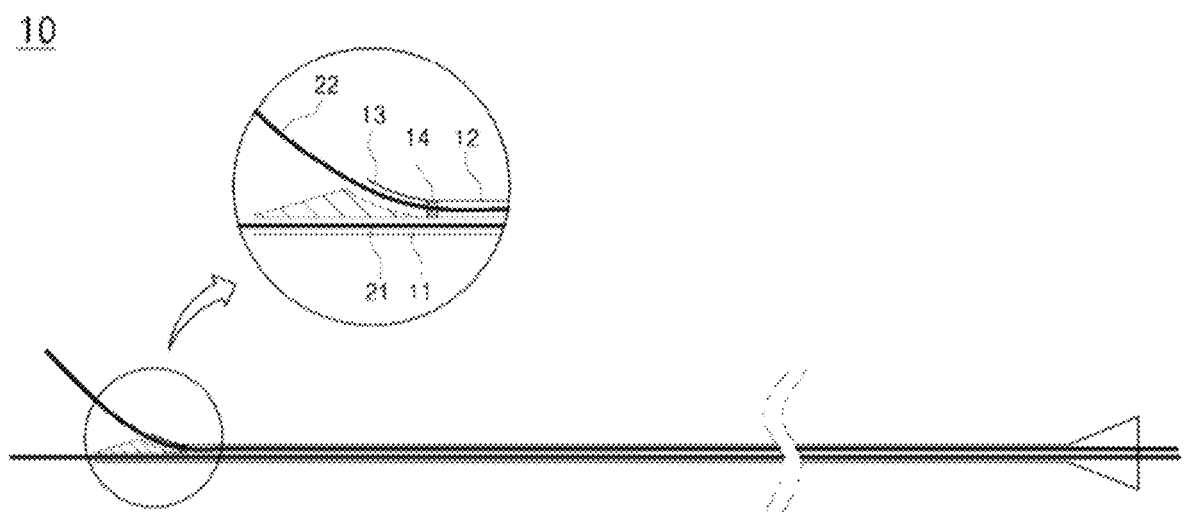
(A)
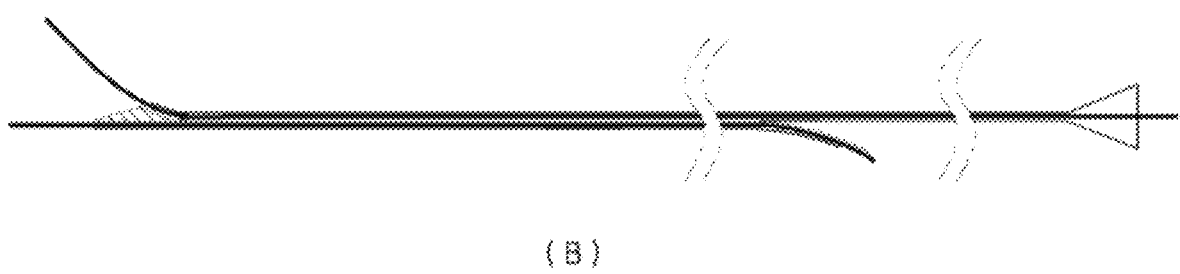
(B)

FIG. 9
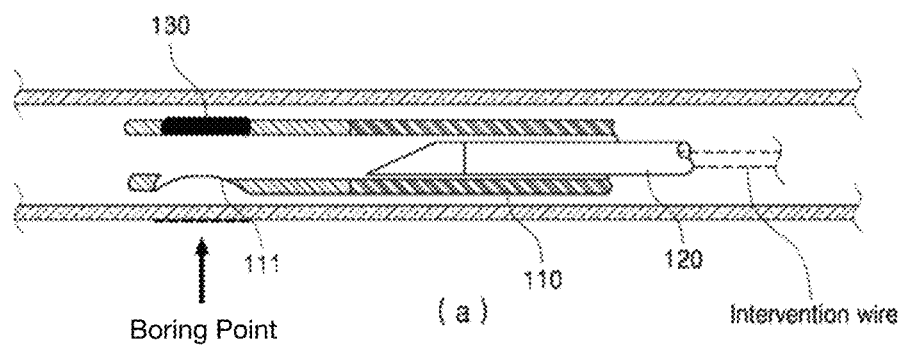
(a)
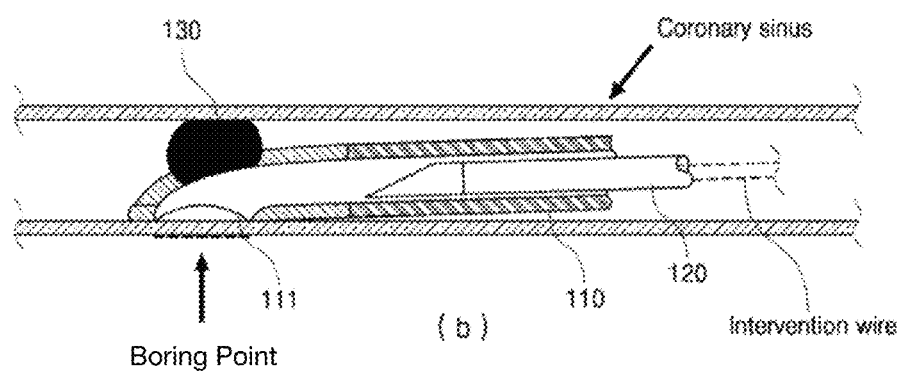
(b)
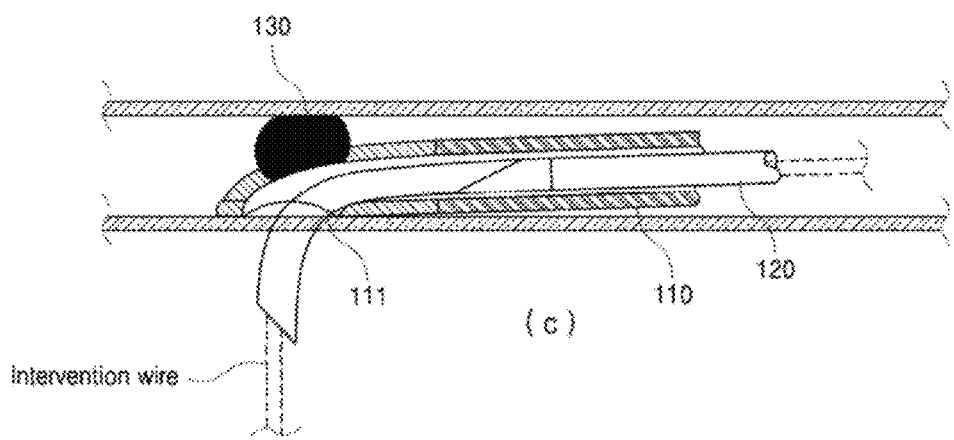
(c)

FIG. 14
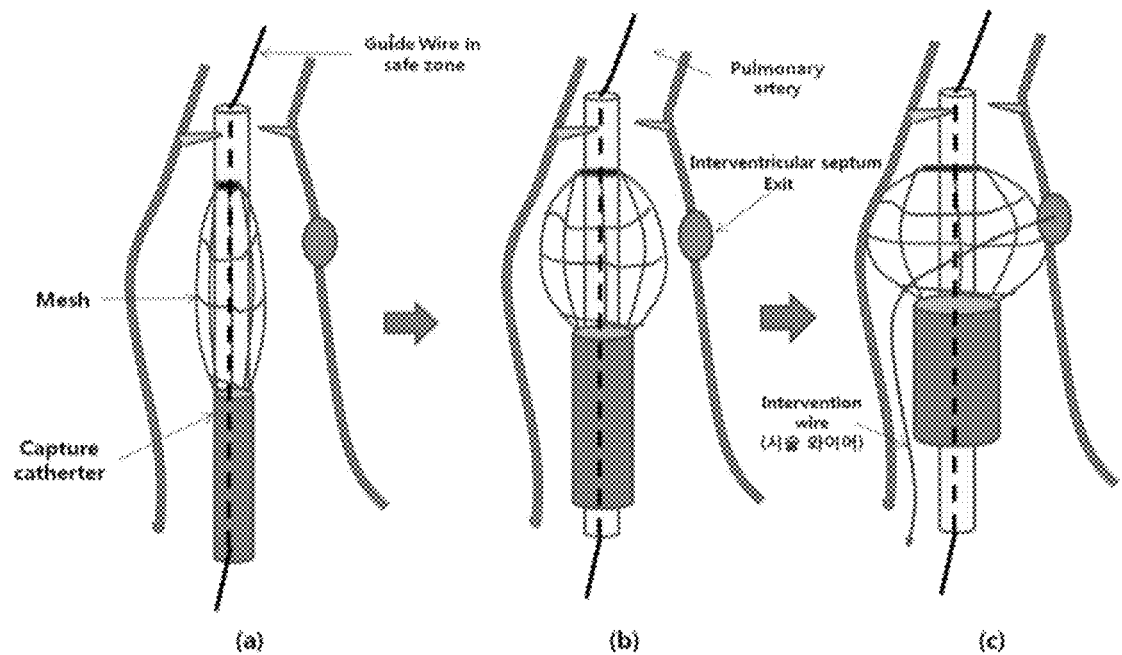
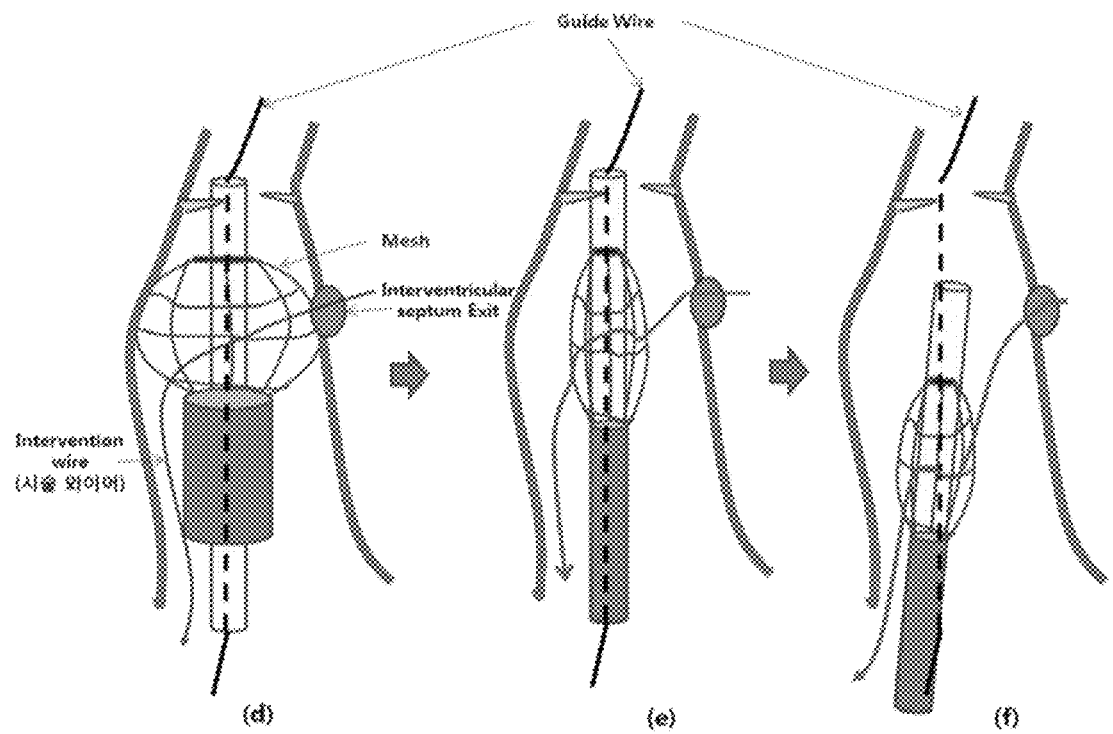

FIG. 19
Comparison of Trans-Coronary Sinus Intraseptal Placing and RVAP
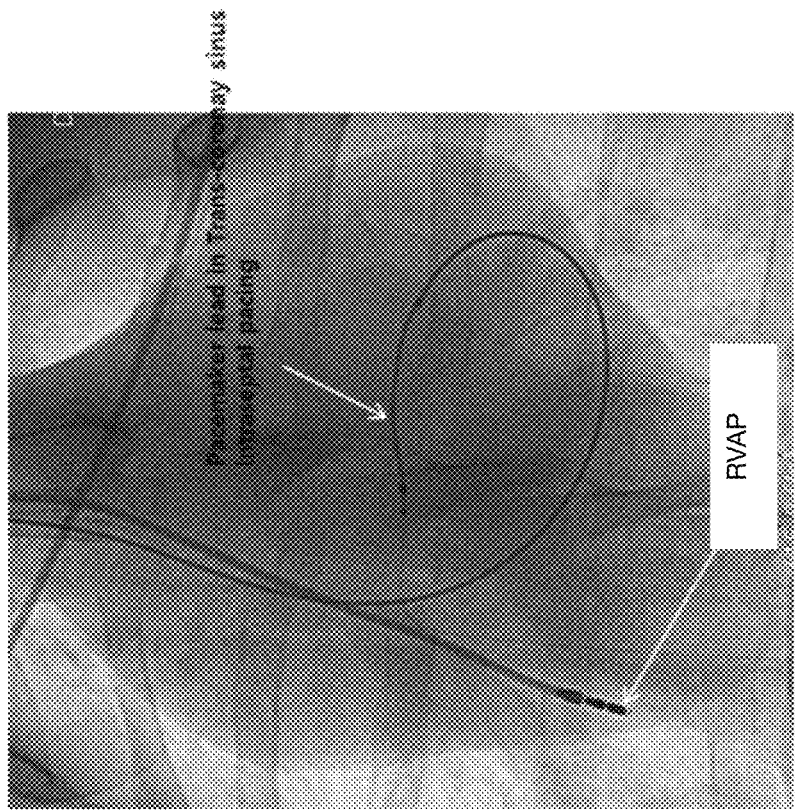
(B)
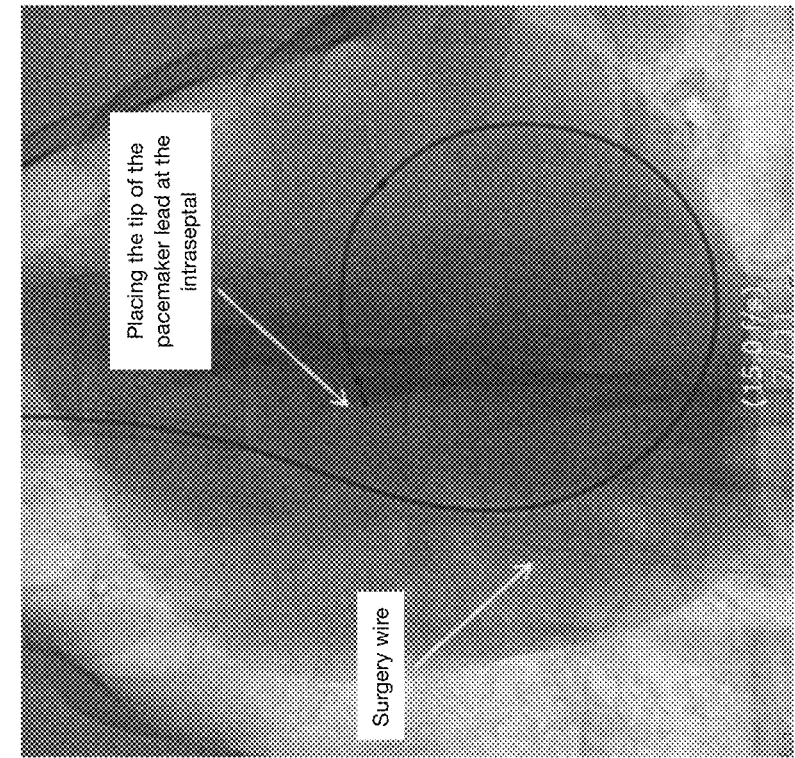
(A)

METHOD FOR POSITIONING TERMINAL END OF PACEMAKER LEAD, WHICH HAS PASSED THROUGH CORONARY SINUS, IN INTERVENTRICULAR SEPTUM

CROSS-REFERENCE TO PRIOR APPLICATIONS

This application is a continuation of U.S. application Ser. No. 15/328,046, filed on Jan. 22, 2017, which was a National Stage patent application of PCT International Patent Application No. PCT/KR2015/006044 (filed Jun. 16, 2015) under 35 U.S.C. § 371, which claims priority to Korean Patent Application Nos. 10-2014-0092789 (filed on Jul. 22, 2014), which are all hereby incorporated by reference in their entirety.

TECHNICAL FIELD

The present invention relates to a method for positioning a tip of a pacemaker lead that has passed through coronary sinus into an interventricular septum. More particularly, it relates to a method, for positioning a tip of a pacemaker lead that has passed through a coronary sinus into an interventricular septum in order to more effectively transmit an electrical stimulus in a treatment using a pacemaker for patients with arrhythmia.

BACKGROUND ART

Since a pacemaker was first introduced by Furman and Rovinson in 1958, the pacemaker has been used as an important device for treating patients with bradyarrhythmia. Recently, a pacemaker is usually used in treatments for arrhythmia such as complete atrioventricular block, high degree atrioventricular block, and sinus node dysfunction accompanied by symptoms. A treatment using a pacemaker is a method that artificially provides an electrical stimulus when an electrical stimulus is not normally transmitted to a heart.

FIG. 1 is a view of a conduction system of a heart, in which FIG. 1(A) shows a flow in a conduction system, and FIG. 1(B) shows a waveform in an electrocardiogram, and FIG. 1(C) illustrates the relationship between a conduction process and a waveform.

According to the conduction of the heart, an electrical stimulus is transmitted to the overall ventricles through a conduction pathway after passing through a sinoatrial (SA) node, an atrioventricular (AV) node in atriums and then passing through the bundle of His and a bundle branch in ventricles. Transmission of stimulus in a ventricle is made by a His-Purkinje system.

In an electrocardiogram, a QRS-complex is generated by a depolarization process of ventricular muscles, the first downward wave following a P-wave is called a Q-wave, the first upward wave is called an R-wave, and the downward wave following the R-wave is called an S-wave. The width of the QRS means the time taken for electricity to be conducted throughout the entire ventricles. The width of the QRS is within about 0.12 seconds (around about 90 ms) in a normal state, but when it is 0.12 seconds or more, it indicates the presence of an interventricular conduction defect including blocks.

A pacemaker is composed of a generator and a lead. The generator supplies power and includes a computer, so it supplies power, if necessary, or suspends the power by checking the state of electricity flowing into a heart through the lead. The lead transmits electricity from the generator to the heart.

FIG. 2 shows the treatment performed at present by a pacemaker.

According to a common treatment that is performed by a pacemaker at present, the tip of the lead of a pacemaker is inserted and fixed in the apex of the right ventricle (RV apex) of ventricles and then electrical stimulus is provided. This is called right ventricular apical pacing (RVAP).

As for RVAP, the electrical stimulus at the RV apex is not transmitted through the conduction system that is a special tissue structure for quickly transmitting electrical stimulus in a ventricle, but transmitted through cariomyocytes of the ventricle that relatively slowly transmit electrical stimulus, so it takes long time for the electrical stimulus to spread through the entire ventricle. It means that the QRS width increases in an electrocardiogram and is called "Wide QRS". That is, the QRS passing through the RVAP is about 160 ms, which is considerably delayed as compared with 90 ms for a normal case.

The Wide QRS causes non-uniformity of motion of ventricles, that is, ventricular desynchronization, so it causes a side effect of loss of the ventricular function. Many studies for obtaining narrower QRS by giving electrical stimulus to portions close to a conduction system at an interventricular septum have been conducted to overcome the side effect.

Representatively, a method of positioning the tip of a pacemaker lead at a right ventricular basal septum and applying electrical stimulus around the conduction system has been attempted. This is called right ventricular septal pacing (RVSP). The RVSP is most usually used at the interventricular septum of a right ventricular outflow tract (RVOT).

The RVSP theoretically compensates for the defects of the RVAP, but in the actual operation it is difficult to accurately position the lead of a pacemaker at the interventricular septum around the RVOT and the lead may be separated or moved, so the operation itself is difficult and accordingly it is not generally used. The RVSP has another characteristic that positions the lead tip at an interventricular septum, but stimulates not the inside, but the outer side of the interventricular septum, and it is known that the RVSP is less effective than the method of stimulating the endocardium or the center of an interventricular septum.

Another method of obtaining a narrower QRS is applied to a case when a patient with heart failure accompanied by ventricular insufficiency has a wide QRS in an electrocardiogram. This method uses two leads, and positions a lead at an RV apex and applies electrical stimulus and positions the other lead at a left lateral vein and applies electrical stimulus to a side of the left ventricle. That is, it is a treatment for securing a narrower QRS by simultaneously applying electrical stimulus to the RV apex and the side of the left ventricle. It is called "Cardiac Resynchronization Therapy (CRT)".

The CRT is known as a very effective and remarkable treatment when a patient with heart failure has LBBB (left bundle branch block), etc. However, the CRT has a defect that it has to use two leads for stimulating ventricles in order to obtain a narrower QRS.

According to the treatments used up to now, if it possible to directly apply electrical stimulus to the interventricular septum where the conduction system of ventricles are positioned when applying electrical stimulus to the ventricles, it is possible to obtain a narrower QRS and the transmission direction of the electrical stimulus can apply biological electrical stimulus, so it is possible to overcome the problems with the RVAP and expect good effects from some patients who need CRT.

According to various recent studies on animals, it has been reported that it is possible to further compensate for the defects of the RVAP by directly applying electrical stimulus to the interventricular septum and it is also possible to give help for ventricular insufficiency that needs the CRT. Intraseptal pacing that can apply direct electrical stimulus to an interventricular septum has been attempted, and methods by forcibly positioning the lead of a pacemaker into the interventricular septum directly through the left ventricle from the right ventricle have been disclosed in US2010/0298841 and US 2013/0231728. These methods have high invasion depth that causes an artificial loss of interventricular septum between the left and right ventricles, have a high possibility of tearing surrounding tissues during the operation, and have a high possibility of causing an embolism due to air or blood clots. Further, the methods have many dangers and limits, for example, it can locally approach the middle portion or the apex of ventricles rather than the base which is preferable.

Accordingly, it is required to study a method that can more safely and simply obtain a narrower QRS by directly applying electrical stimulus to the conduction system of a ventricle.

DISCLOSURE

Technical Problem

In order to solve the problems, an object of the present invention is to provide a method, for applying direct electrical stimulus to an interventricular septum, where the conduction system of the heart is positioned, and more safely and simply positioning the tip of a pacemaker lead passing through a coronary sinus into the interventricular septum in order to more effectively apply electrical stimulus in a treatment using a pacemaker.

In detail, an object of the present invention is to provide a method, for applying direct electrical stimulus to an interventricular septum, where the conduction system of the heart is positioned, and more safely and simply positioning the tip of a pacemaker lead passing through a coronary sinus into the interventricular septum without safety problems, thereby overcoming defects of wide QRS pacing due to RVAP of the related art, removing difficulty in an operation that is a defect of the RVAP, improving a way of applying electrical stimulus, and achieving treatment effect with only one lead without using two leads that is a defect of CRT.

Technical Solution

In order to achieve the objects of the present invention, a method of positioning a tip of a pacemaker lead, which has passed through a coronary sinus, into an interventricular septum, in order to effectively transmit electrical stimulus, includes: inserting into a intervention wire through a superior vena cava and a coronary sinus to pass through the interventricular septum and then guiding the intervention wire to an inferior vena cava; and positioning the tip of the lead into the interventricular septum by inserting the pacemaker lead along the intervention wire.

According to an embodiment of the present invention, an apparatus for positioning a tip of a pacemaker lead, which has passed through a coronary sinus, into an interventricular septum where a conduction system of a heart is positioned, in order to effectively transmit electrical stimulus, includes: a intervention wire connected through a inferior vena cava, a coronary sinus, an interventricular sinus, a right ventricle, and an inferior vena cava; a surgical catheter passing through the inferior vena cava and a safe zone to capture the intervention wire positioned in the right ventricle; and a pacemaker lead inserted along the intervention wire such that the tip is positioned in interventricular septum tissues.

The apparatus further includes a balloon-tipped guiding catheter having a hole therein for passing the intervention wire and having a balloon that is formed at a front end to be inflated by air from the outside so that a septal vein positioned at the interventricular septum is easily found by blocking the coronary sinus.

Advantageous Effects

As described above, according to the method of positioning the tip of a pacemaker lead passing through a coronary sinus into an interventricular septum, the pacemaker lead is positioned into the interventricular septum using a septal vein on the basis of the coronary sinus and then electrical stimulus is applied. Accordingly, it is possible to (1) overcome the defects of wider QRS pacing due to RVAP of the related art and (2) expect treatment effect with only one lead without using two leads for patients to whom narrower QRS can be applied only with septal pacing of patients who need CRT of the related art.

Further, according to the present invention, as in the method disclosed in US 2010/0298841 A1 and US 2013/0231728 A1, it is possible to minimize the danger of an operation by positioning the lead of a pacemaker through a relatively simple operation in a vein, using a path that is maximally naturally formed along an interventricular septum without using a high-dangerous and non-physiological operation that artificially open a left ventricle for high-pressure arteries and a right ventricle under low pressure.

DESCRIPTION OF DRAWINGS

FIG. 1 is a view of a conduction system of a heart, in which

FIG. 2 shows the treatment performed at present by a pacemaker.

FIG. 3 is a flowchart illustrating a method of positioning the tip of a pacemaker lead, which as passed through a coronary sinus, into an interventricular septum, in accordance with an embodiment of the present invention.

FIG. 6 is a schematic cross-sectional view of a dual lumen catheter according to an embodiment of the present invention, in which (A) shows the case when the first tube and the second tube have the same length and (B) shows the case when the first tube and the second tube have different lengths.

FIGS. 7 and 8 are partial cut views of a heart for showing a process of boring the interventricular septum using a dual lumen catheter according to an embodiment of the present invention, in which FIG. 7 shows the case when the advancing direction of a support wire is an RVIT direction and FIG. 8 shows the case when the advancing direction of the support wire is an RV epicardial vein direction.

FIG. 9 is a view showing a process of boring the interventricular septum using a needle type lumen catheter according to an embodiment of the present invention.

FIGS. 10 and 11 are anatomical pictures showing actual examples of a safe zone and an unsafe zone that a guide wire of the present invention passes through.

FIG. 14 is a view illustrating a process of capturing a intervention wire using a mesh of a capture catheter of the present invention.

FIG. 19A is a picture showing a tip of a pacemaker lead inserted in tissues of an interventricular septum in accordance with an embodiment of the present invention and FIG. 19B is a picture showing a pacemaker lead according to CS based intraseptal pacing of the present invention and a pacemaker lead positioned at an RV apex according to an RVAP of the related art.

BEST MODE

The present invention relates to a method that positions a tip of a pacemaker lead into an interventricular septum after passing the tip through a coronary sinus in order to more effectively transmit electrical stimulus in a treatment using a pacemaker. That is, the method positions the tip of a pacemaker lead into an interventricular septum to directly apply electrical stimulus to an interventricular septum where the conduction system of the heart is positioned.

The RVSP described above positions the tip of a pacemaker lead on the outer side of the interventricular septum rather than the inside, so it is less effective in terms of transmitting electrical stimulus in an interventricular septum when theoretically transmitting electrical stimulus to the conduction system in the interventricular septum.

The inventor(s) has developed a method and an apparatus that can position the tip of a pacemaker lead using a wire that passes through a superior vena cava, a coronary sinus, and an inferior vena cava.

A method of positioning the tip of a pacemaker lead of the present invention includes: i) positioning a intervention wire inserted through a superior vena cava and a coronary sinus (CS) into the right ventricle of the heart through an interventricular septum; ii) inserting a surgical catheter inserted in an inferior vena cava into the right ventricle through the right atrium and a safe zone of the tricuspid valve and then capturing the intervention wire using a capturing unit of the surgical catheter; iii) pulling out the surgical catheter toward the inferior vena cava and pulling out the intervention wire captured by the surgical catheter toward the interior vena cava; and iv) positioning the tip of the lead into the interventricular septum by holding both ends of the intervention wire and inserting the lead of the pacemaker along the intervention wire. In other words, the method largely includes: passing a intervention wire through an interventricular septum after passing it through a superior vena cava and a coronial sinus and then guiding the intervention wire to an inferior vena cava; and positioning the tip of a lead into the interventricular septum by inserting the lead of the pacemaker along the intervention wire.

A method of positioning a tip of a pacemaker lead into an interventricular septum of the present invention will be described hereafter in more detail with the accompanying drawings.

Figure 1A:
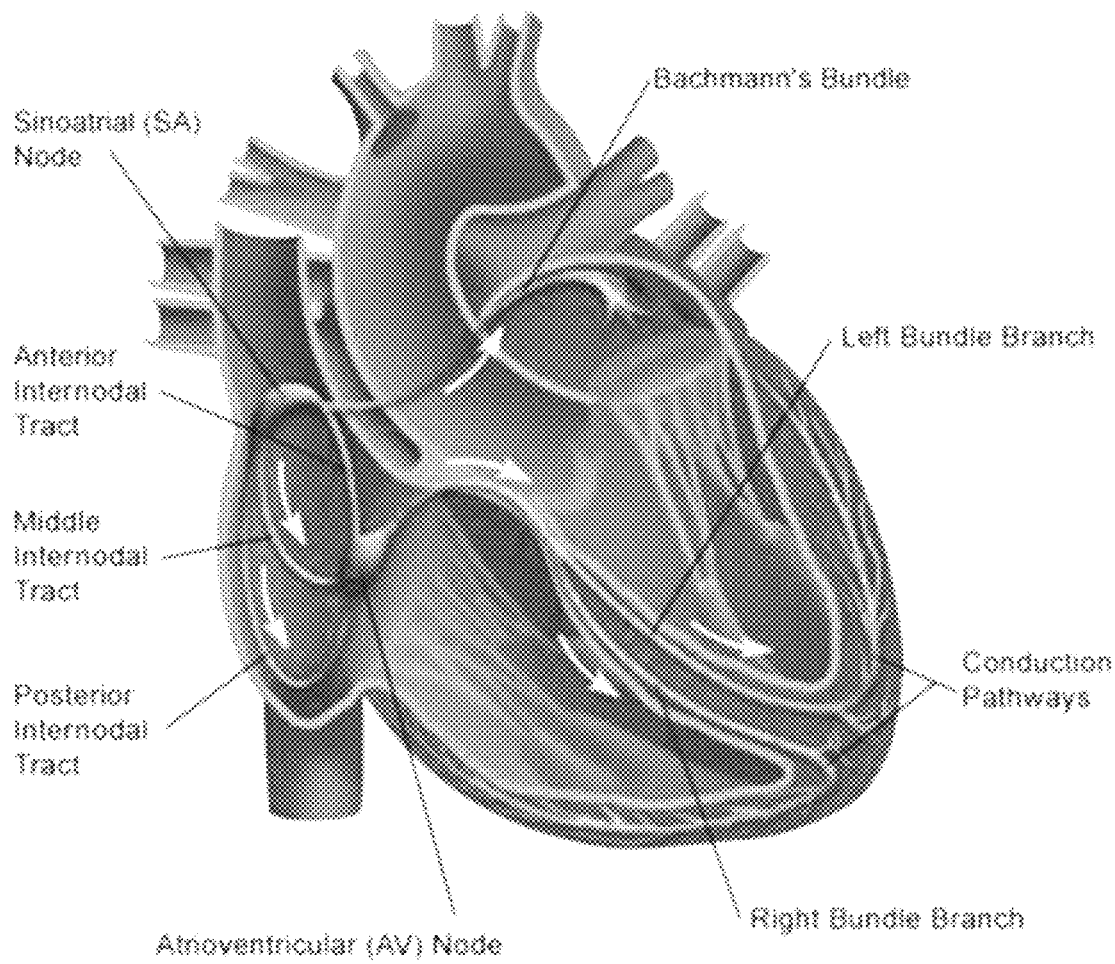
FIG. 1(A) shows a flow in a conduction system.
Figure 1B:
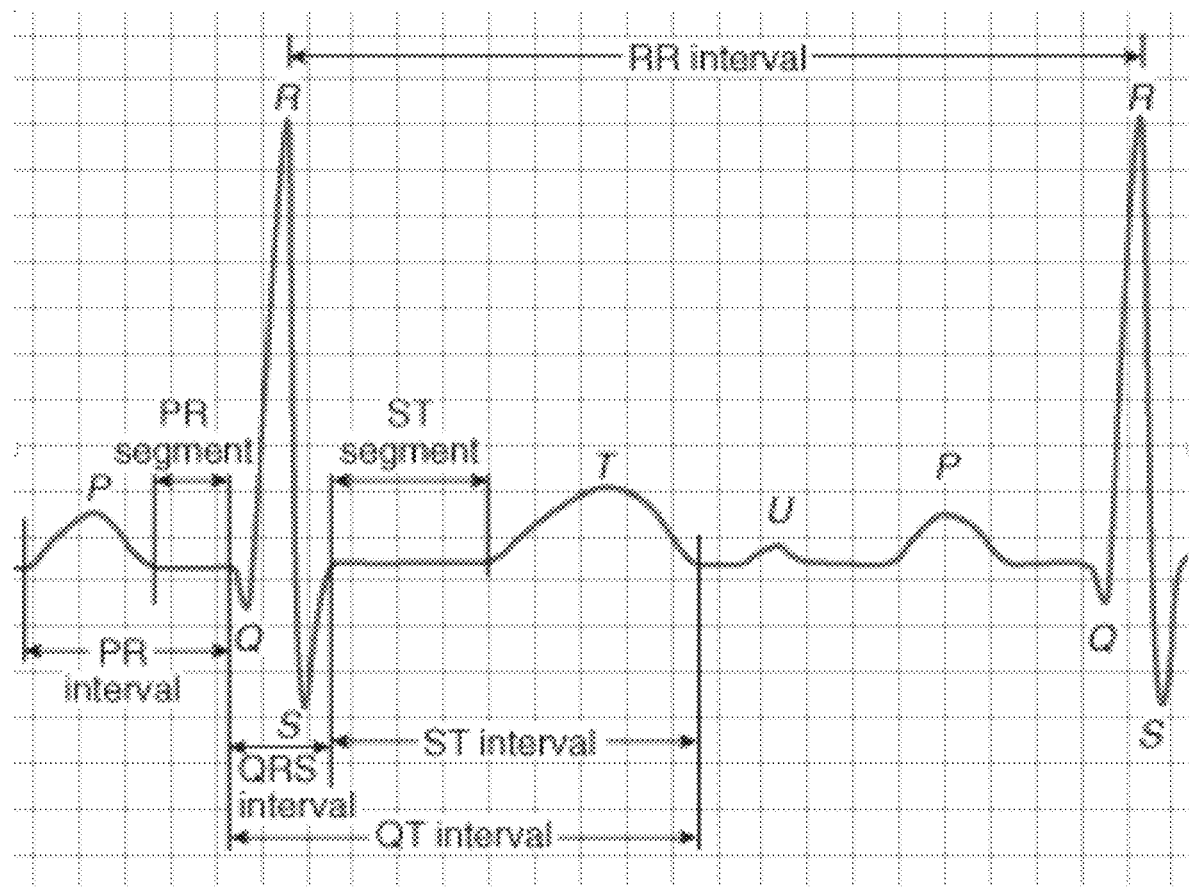
FIG. 1(B) shows a waveform in an electrocardiogram.
Figure 1C:
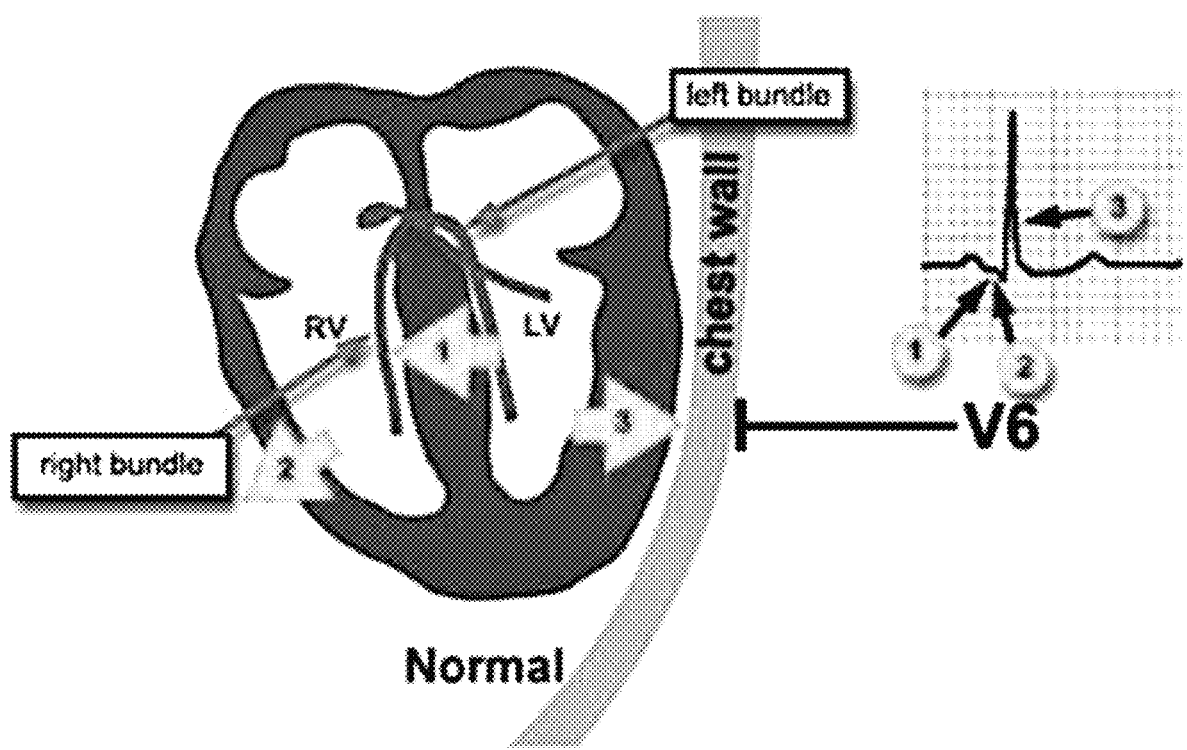
FIG. 1(C) illustrates the relationship between a conduction process and a waveform.
Figure 4:
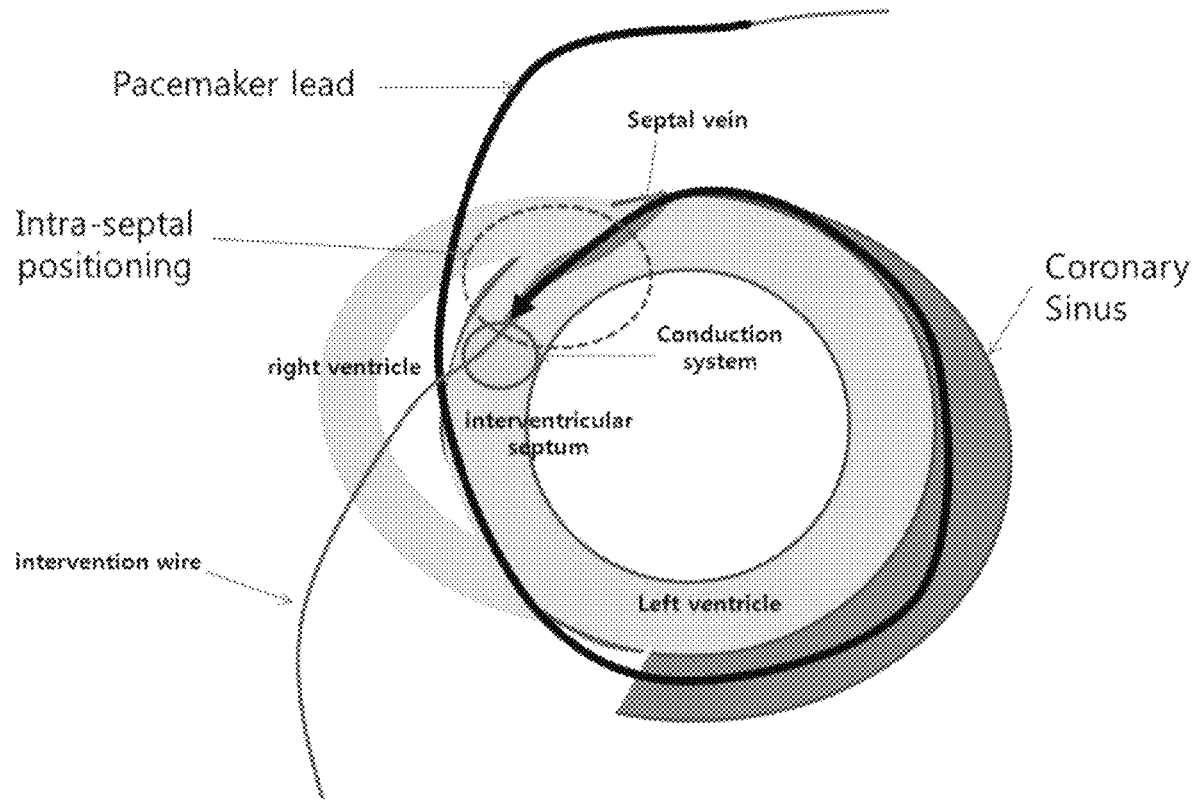
FIG. 4 is a schematic diagram illustrating the method of positioning the tip of a pacemaker lead, which as passed through a coronary sinus, into an interventricular septum, in accordance with an embodiment of the present invention.

FIG. 3 is a flowchart illustrating a method of positioning the tip of a pacemaker lead into an interventricular septum in accordance with an embodiment of the present invention and FIG. 4 is a schematic diagram illustrating a method of positioning the tip of a pacemaker that has passed through a coronial sinus into an interventricular septum.

Referring to FIGS. 3 and 4, i) a step (S10) of positioning a intervention wire inserted through a superior vena cava and a coronary sinus SC into the right ventricle of the heart through an interventricular septum is shown.

The intervention wire (intervention wire) is inserted through the superior vena cava and the coronary sinus and guided into the inferior vena cava through the interventricular septum, and then the upper and lower portions are fixed by a surgeon, thereby supporting a pacemaker lead such that the pacemaker lead is inserted through the coronary sinus and inserted into the interventricular septum. Preferably, the intervention wire is a intervention wire of about 0.014". The intervention wire guides the pacemaker lead, so it is also called a pacemaker lead guide wire.

The intervention wire is moved into the interventricular septum through a septal vein that is an appropriate ventricular base. However, it is generally difficult for a surgeon to recognize the septal vein. Accordingly, there is a need for a balloon-tipped guiding catheter having a hole therein for passing a intervention wire. The balloon-tipped guiding catheter, which is a catheter having a balloon at the front (top) end, blocks a coronary sinus by expanding the balloon by injecting air from the outside after being inserted through a superior vena cava and the coronary sinus. Accordingly, the blood current in the coronary sinus is blocked, whereby the pressure in the coronary sinus increases and the coronary sinus expands. Thereafter, the septal vein in the interventricular septum is found by projecting a pressurized venogram. The intervention wire is passed through the interventricular septum by external force after being inserted into the septal vein through the hole of the balloon-tipped guiding catheter.

Figure 5:
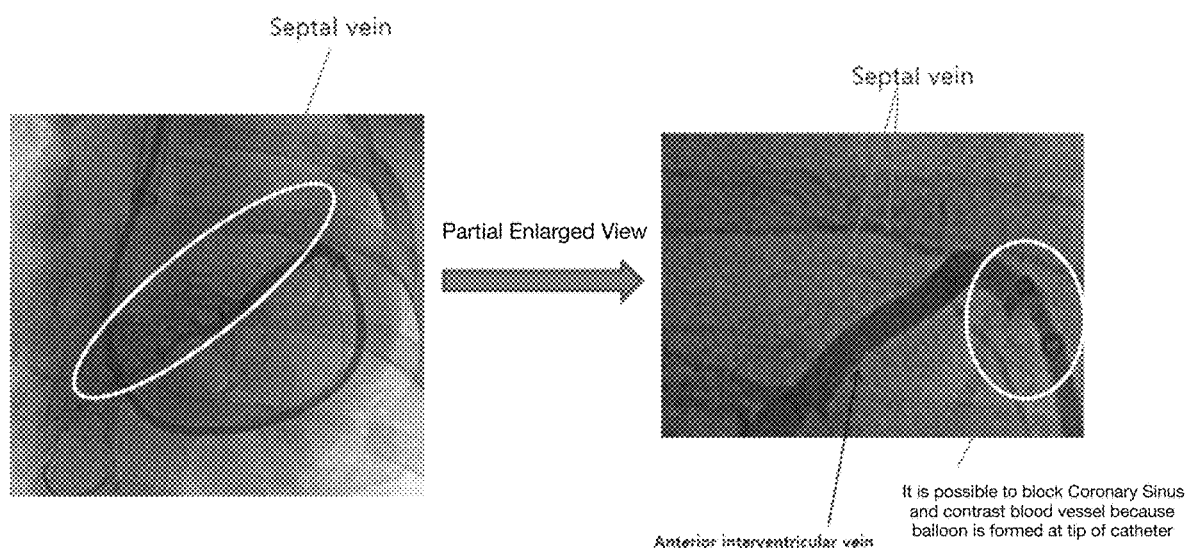
FIG. 5 is a picture of a pressurized septal venogram when a coronary sinus is blocked by a balloon catheter according to an embodiment of the present invention.

FIG. 5 is a picture of a pressurized septal venogram when a coronary sinus is blocked by a balloon catheter according to an embodiment of the present invention. In detail, FIG. 5 is a picture obtained in the following embodiment.

After the intervention wire passes through the interventricular septum, the balloon-tipped guiding catheter is removed outside and the tip of the intervention wire is positioned in the ventricle.

On the other hand, when the septal vein is not seen or is short, or it is difficult to bore the interventricular septum through the septal vein, a specific interventricular septum lumen catheter is required. The interventricular septum lumen catheter may be a dual lumen catheter having two tubes for inserting two wires and a needle type lumen catheter using a needle.

That is, in general, it is possible to directly bore an interventricular septum with a intervention wire without a specific interventricular septum lumen catheter by pointing the tip of the intervention wire, but an interventricular septum lumen catheter is required in the exceptional case described above.

First, the dual lumen catheter may be used when it is not preferable to bore an interventricular septum after passing a intervention wire through a septal vein.

Figure 7:
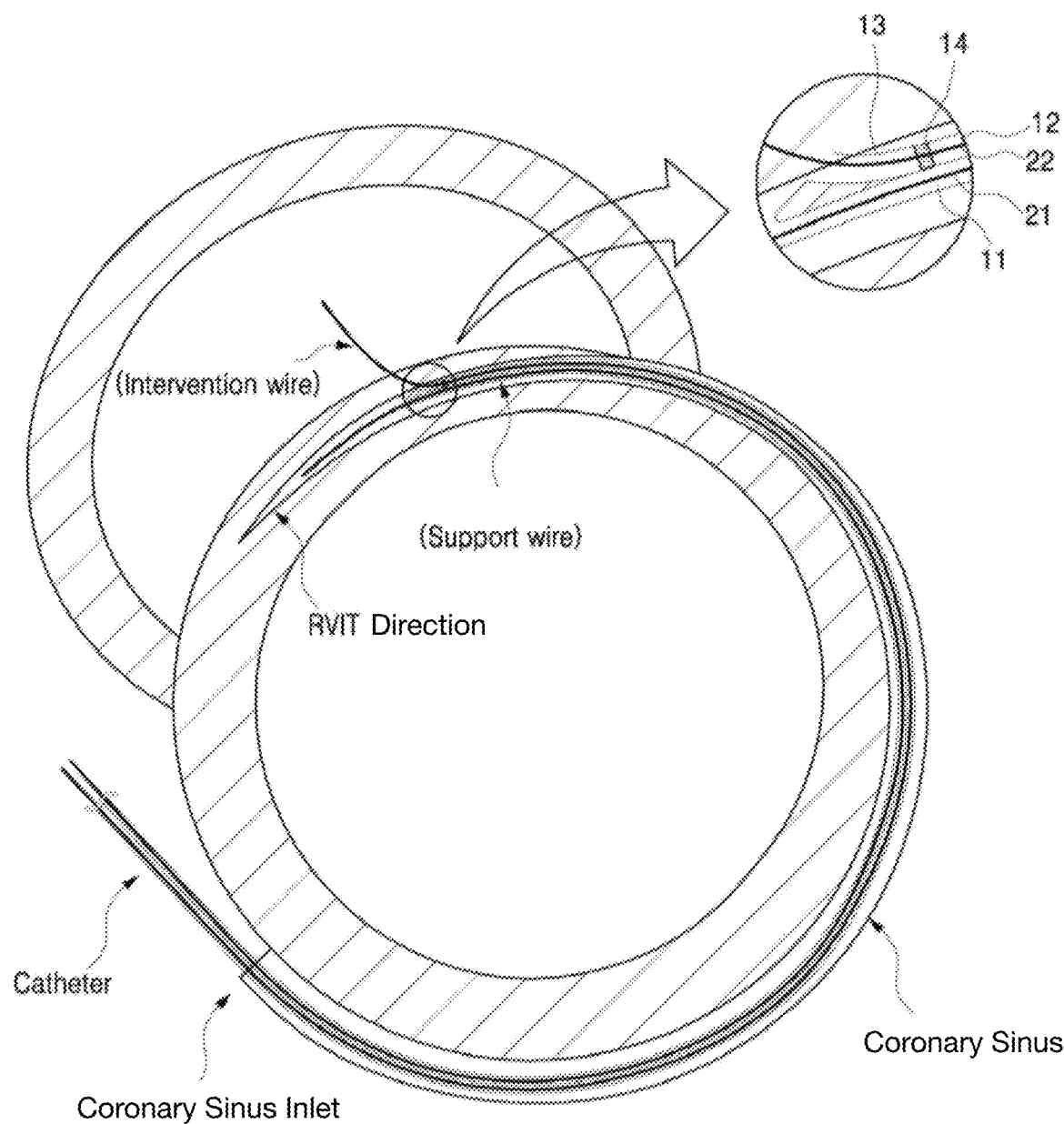
Figure 8:
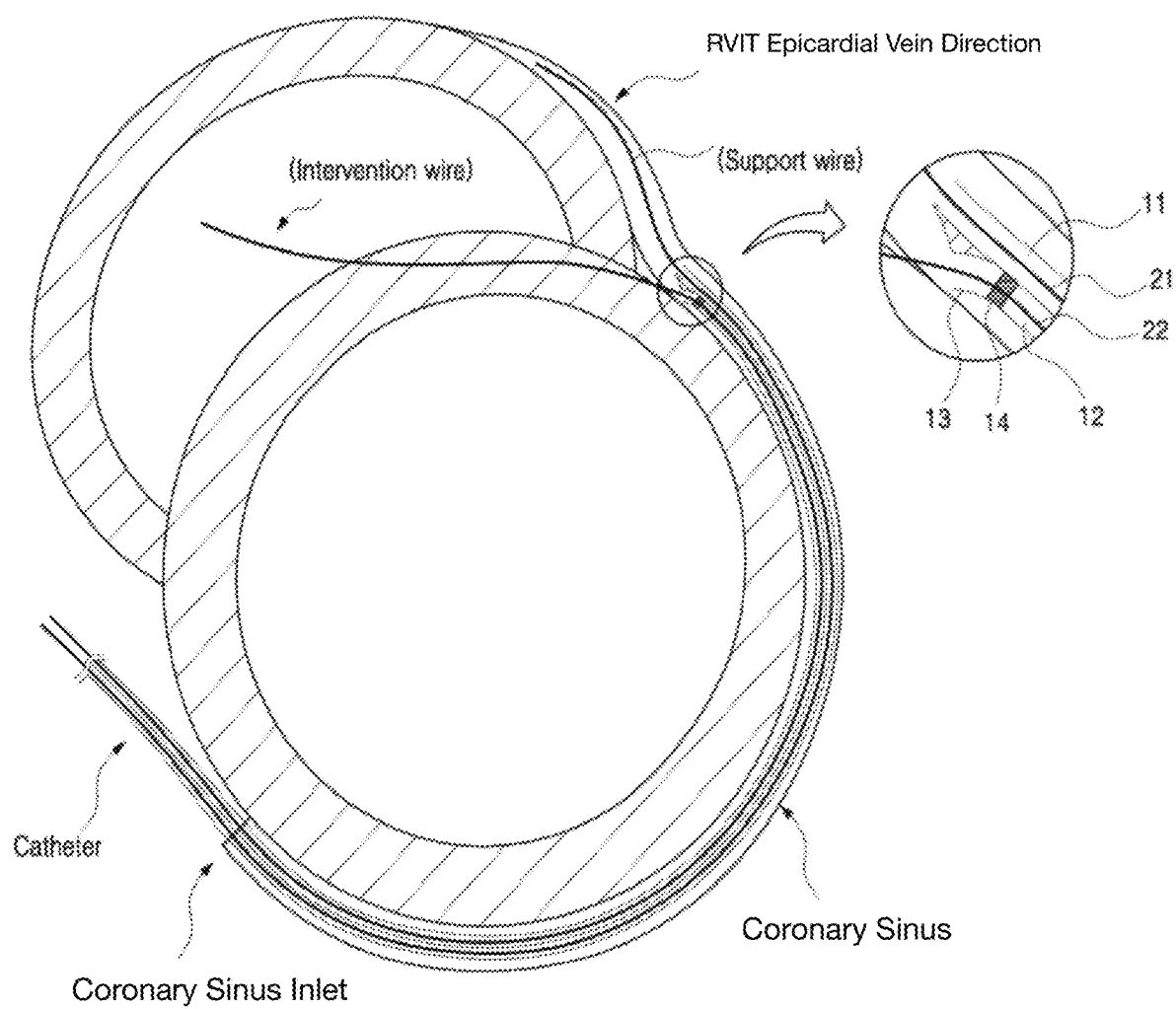

FIG. 6 is a schematic cross-sectional view of a dual lumen catheter according to an embodiment of the present invention, in which (A) shows the case when the first tube and the second tube have the same length and (B) shows the case when the first tube and the second tube have different lengths, and FIGS. 7 and 8 are partial cut view of a heart for showing a process of boring an interventricular septum using a dual lumen catheter according to an embodiment of the present invention, in which FIG. 7 shows the case when the advancing direction of a support wire is an RVIT direction and FIG. 8 shows the case when the advancing direction of the support wire is an RV epicardial vein direction.

Referring to FIG. 6, the dual lumen catheter is composed of a first tube in which a support wire is inserted and a second tube in which a intervention wire is inserted. The first tube 11 and the second tube 12 of the lumen catheter is fixed in contact with each other, in which two tubes may be in contact with each other or one tube may be divided into two spaces by a film. The first tube 11 and the second tube 12 may be the same or different in length. FIG. 6A shows the case when the first tube and the second tube have the same length and FIG. 6B shows the case when the first tube and the second tube have different lengths. When it is not required to make the support wire longer than the intervention wire, the first tube and the second tube are made different in length by making the first tube shorter as in FIG. 6B.

The support wire 21 inserted in the first tube 11 supports the intervention wire 22 inserted in the second tube 12 when the intervention wire 22 bores an interventricular septum, that is, functions as a support that prevents the intervention wire 22 from being pushed back when the intervention wire 22 bores an interventricular septum. The intervention wire 22, as described above, is connected to an inferior vena cava after passing through the interventricular septum, thereby guiding or supporting a pacemaker lead that is inserted later.

Since the support wire functions as a support and the intervention wire passes through the interventricular septum, the support wire may be softer than the intervention wire in many cases.

The lumen catheter has a radiopaque marker 14. The radiopaque marker 14 is provided to help the intervention wire bore an interventricular septum by finding the location of the lumen catheter through a display. That is, the radiopaque marker 14 is provided for easy boring of an interventricular septum.

Meanwhile, an inclined guide 14 having a predetermined angle is formed at the second tube tip, that is, the exit of the second tube of the lumen catheter. This is for the intervention wire 22 to be able to bore an interventricular septum through the second tube 12.

Referring to FIGS. 7 and 8 to explain the process of boring, the lumen catheter is inserted into a coronary sinus and then the support wire 21 is inserted into the first tube 11 of the lumen catheter. Alternatively, the support wire may be inserted first and then the lumen catheter is inserted, or the lumen catheter may be inserted with the support wire inserted therein.

In general, the support wire 21 is moved along various paths, depending on the characteristics of the wire and the shape of the septal vein, for example, in a right ventricular inflow tract (RVIT) direction in accordance with the connection direction of the coronary sinus. The intervention wire may be easily taken out of the preferable exit of the right ventricle such as the RVIT without help of other devices (other wires or other catheters), but is not guided to the preferable exit in many cases. That is, the ideal wire exits are different for each patient. When it is difficult to bore an interventricular septum only with a intervention wire, the operation becomes easy by using a support wire, so a dual lumen catheter is useful in this case.

The support wire 21 is inserted, and then the lumen catheter is moved to an appropriated position in an interventricular septum and the intervention wire 22 is inserted into the second tube 12 of the lumen catheter. It is possible to find the location where the intervention wire comes out, that is, the location of the tip of the second tube through the radiopaque marker 14 and the location is the "interventricular septum-through start point".

It is possible for a surgeon to relatively easily find whether the support wire has been inserted in the right ventricular inflow tract (RVIT) (septal vein) direction or the RV epicardial vein direction by checking the shape of the heart, the positions of blood vessels, and the positions of the wires while performing an angiogram. Accordingly, the surgeon can find the location of the support wire and bores the interventricular septum by pushing the intervention wire, as shown in FIGS. 7 and 8.

The intervention wire that has passed through the interventricular septum is guided to the right ventricle. Preferably, the tip of the intervention wire is pointed or made of a hard material to easily bore the interventricular septum. Accordingly, the intervention wire is guided to the right ventricle and then the lumen catheter and the support wire are removed.

A needle lumen catheter that is another type of lumen catheter using a needle can be used when the septal vein of an interventricular septum is not easily found even by contrast.

FIG. 9 is a view showing a process of boring an interventricular septum using a needle lumen catheter according to an embodiment of the present invention.

Referring to FIG. 9, a need lumen catheter is used to bore an interventricular septum using a intervention wire. The needle lumen catheter, which is used to connect an end of a coronary sinus (CS) and the right ventricle to each other by moving through a superior vena cava and a coronary sinus (CS) and then boring the interventricular septum that is the membrane between the coronary sinus (CS) and the right ventricle, is largely composed of a body 110, a needle 120, and a fixture 130.

The body 110 is a hollow tube and has a hole 112 for the needle at an end thereof.

The needle 120 is inserted in the body 110 and can moved forward/backward through the hole 111. The hole 111 is moved to a portion to be bored by inserting the catheter is through a superior vena cava and a coronary sinus and then the needle 120 is moved forward, thereby boring the interventricular septum. The front end of the needle 120 is pointed to be quickly bore the interventricular septum without damaging surrounding tissues. An operation unit for operating the needle 120 at the outside may be further provided to bore the interventricular septum by moving the needle 120 forward/backward.

The fixture 130 is provided to prevent other portions except the portion to be bored from being bored or the needle 120 from being pushed backward such that the portion is not bored at a time when the needle 120 moves forward to bores the interventricular septum. For this purpose, the fixture 130 is positioned to correspond to the hole 111 and then the needle 120 is moved forward, thereby boring the interventricular septum. The fixture 130, in this process, supports the body 110 to prevent the body 110 from being pushed backward.

The fixture 130 may be a balloon that can be inflated by air from the outside, so a pump for injecting air into the balloon from the outside to inflate the balloon may be further provided. When a balloon is used as the fixture 130, it is possible to adjust the air pressure without damaging the coronary sinus (CS) even if the balloon touches the inner side of the coronary sinus.

Meanwhile, an injection unit that can inject a contrast medium into the balloon may be further provided so that the boring position of the interventricular septum can be seen. Since a contrast agent is inserted into the balloon, it is possible to estimate the location of the hole 111 corresponding to the balloon, so it is possible to visually check the boring position and the position to which the needle 120 is moved.

A method of guiding/inserting the intervention wire into the right ventricle using a needle lumen catheter is described with reference to FIG. 9. First, as in (a) of FIG. 9, a needle lumen catheter 100 is moved close to a desired boring position along the coronary sinus (CS). Thereafter, the boring position and the hole 111 are aligned and then fixed by the fixture 130 not to move from the position. The fixture 130 may be a balloon. In other words, air is injected into the balloon with the boring position and the hole 111 aligned.

Accordingly, as in (b) of FIG. 9, the balloon pushes the inner side of the coronary sinus (CS) so that the body is fixed in contact with the boring position. Therefore, it is possible to prevent the boring position from being changed by the body 110 pushed backward when the needle 120 moves forward and bores the boring position later. Further, it is possible to visually find whether the hole 111 is at the accurate position with respect to the boring position when injecting air into the balloon or by injecting a contrast medium later.

After these steps, as in FIG. 9c, the needle 120 is moved in the body and bores the interventricular septum through the hole 111. Thereafter, the intervention wire is inserted and guided to the right ventricle.

There may be many methods of inserting the intervention wire after boring the interventricular septum with the needle. First, there is a method of inserting only the intervention wire after taking the lumen catheter out of the body and then guiding the intervention wire into the right ventricle through the bored portion of the interventricular septum. Second, there is a method of moving the needle 120 backward after boring, moving the intervention wire through the body 110, and then guiding it into the right ventricle. Third, there is a method of guiding the front end of the needle 120 into the right ventricle by moving the intervention wire into the needle 120 after boring the interventricular septum by moving the needle 120 forward. The third method needs a hole at the end of the needle 120 through which the intervention wire can move and the hole is required not to influence the needle boring the interventricular septum.

The lumen catheters (dual lumen catheter and the needle lumen catheter) may be individually used, but may be used as a balloon-tipped guiding catheter by forming a balloon at the front end. When a balloon is coupled to the front end, as described above, it can block the coronary sinus, so the septal vein can be contrasted well.

Next, ii) a step (S20) of inserting the catheter inserted in the inferior vena cava into the right ventricle through the right atrium and the safe zone of the tricuspid valve and then capturing the intervention wire with the capturing unit of the catheter is performed. In this step, there is a need for a safe zone catheter that is supposed to safely pass through the safe zone and a capture catheter that captures the intervention wire guided in the right ventricle in the step i).

When the safe zone catheter and the capture catheter are different, the step ii) is, in detail, composed of a step of inserting the safe zone catheter inserted in the inferior vena cava into the right ventricle through the right atrium and the safe zone of the tricuspid valve, a step of inserting a guide wire through the safe zone catheter, a step of taking out the safe zone catheter with the guide wire maintained at the position, and a step of capturing the intervention wire using the capture catheter inserted along the guide wire.

When the safe zone catheter and the capture catheter are integrated in one unit, that is, when it is a catheter having a blocking member at the upper and a capturing unit under the blocking member, the step ii), in more detail, includes a step of inserting the catheter inserted in the inferior vena cava into the right ventricle through the right atrium and the safe zone of the tricuspid valve and a step of capturing the intervention wire using the capturing unit of the catheter.

That is, the step ii) of the present invention may be a step of pulling out (guiding) the intervention wire inserted in the right ventricle in the step i) toward the inferior vena cava using the catheter inserted through the inferior vena cava.

The "safe zone catheter" inserted through the vena cava is supposed to safely pass through the "safe zone" in the heart, that is, the "safe zone catheter" means a catheter that safely passes through the safe zone without injuring the heart after being inserted from the inferior vena cava.

The catheters or the wire inserted through the inferior vena cava should not injure the structures in the heart. That is, the catheters and the wires should be inserted into a round space surrounded by the subvavular structure such as the leaflet of the tricuspid valve, the chordae of the tricuspid valve, and the papillary, and a moderator band. The virtual round space is called a "safe zone". In order to discriminate this space from a safe zone, it is called an unsafe zone, which means a space that is not safe whereby the human body (heart) can be injured.

Figure 10:
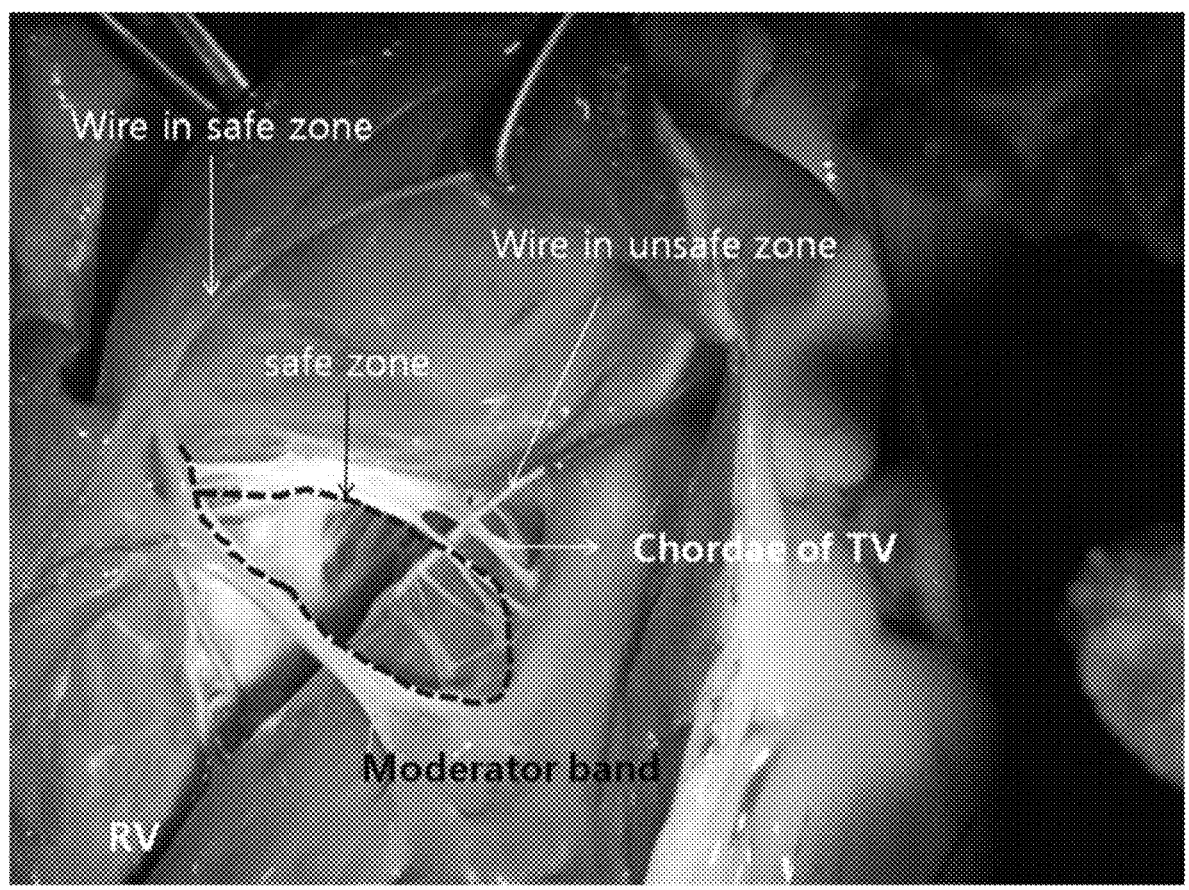
Figure 11:
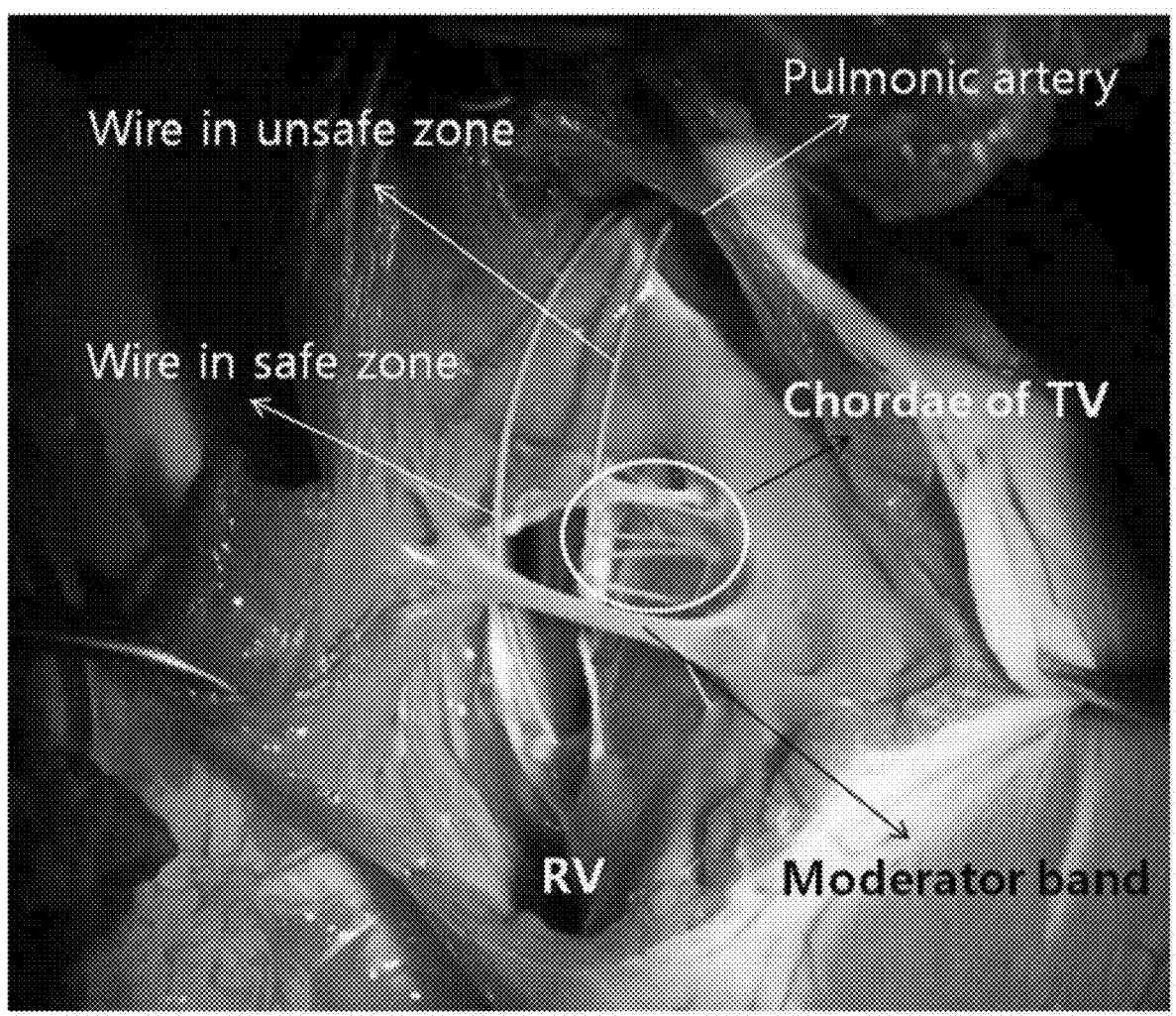

FIGS. 10 and 11 are anatomical pictures showing actual examples of a safe zone and an unsafe zone that a guide wire of the present invention passes through.

In FIGS. 10 and 11, a safe zone and an unsafe zone are clearly discriminated. When a wire or a catheter passes through the unsafe zone, the heart tissues may be seriously injured, so the wire or the catheter should pass through the safe zone. Accordingly, it is required to make sure that a catheter or a wire that is inserted through the inferior vena cava can pass through the safe zone, that is, a catheter or a wire passes through the safe zone.

The catheter that is inserted through the inferior vena cava is called a "safe zone catheter" in terms that it is a catheter for checking whether a wire passes through a safe zone, that is, for safely passing a wire through a safe zone in order to pass the wire through the safe zone in the heart.

The safe zone catheter has a blocking member at the end. The blocking member is a member that locks the catheter when passing through an unsafe zone of the tricuspid valve, but allows the catheter to freely pass through a safe zone of the tricuspid valve so that the catheter can safely pass through the safe zone that does not injure the tricuspid valve. That is, the safe zone catheter can pass through only the safe zone, not the unsafe zone, by the blocking member.

The blocking member may be in the shape of a balloon or a pig tail.

Figure 12:
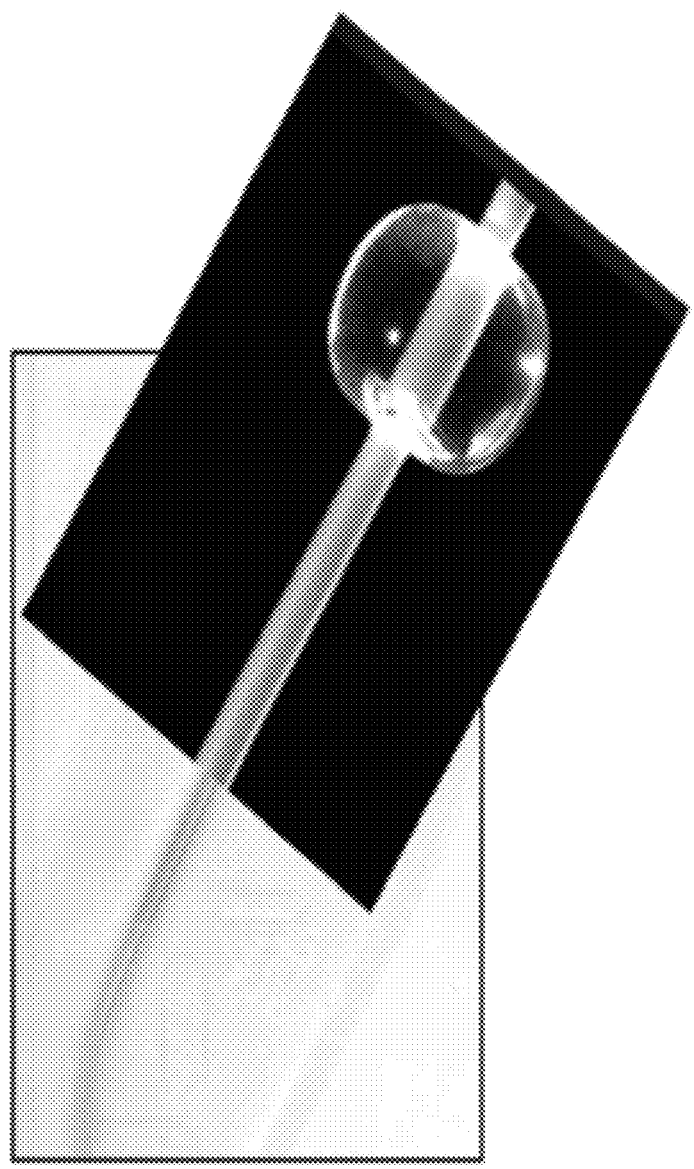
FIG. 12 shows an example of a safe zone catheter having a balloon and FIG. 13 shows an example of a safe zone catheter having a pig tail-shaped blocking member.
Figure 13:
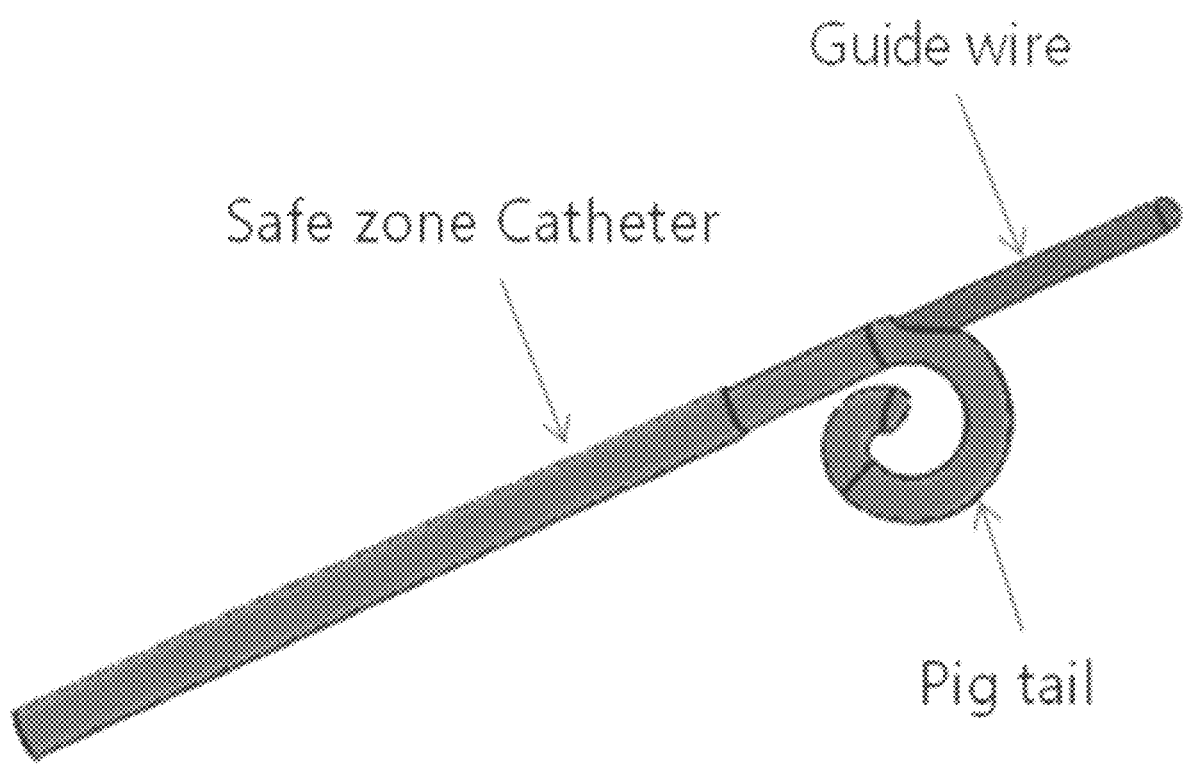

FIG. 12 shows an example of a safe zone catheter having a balloon and FIG. 13 shows an example of a safe zone catheter having a pig tail-shaped blocking member.

The safe zone catheter having a balloon at the end is inserted through an inferior vena cava and then the balloon is inflated by injecting air from the outside, whereby it can pass through only a safe zone and not an unsafe zone. In other words, when the balloon is inserted into an unsafe zone, it cannot be further moved forward into the heart. That is, when the balloon cannot be easily moved forward, it is pulled out and then moved forward until it can pass through a pulmonary artery through a safe zone, so the catheter can safely pass through the safe zone. This method is used in the same way when the blocking member has the shape of a pig tail.

A guide wire is inserted into the right ventricle along the safe zone catheter. That is, a hole is formed in the safe zone catheter, so the guide wire is inserted through the hole.

The term 'guide wire' is given because it is a wire that is inserted to guide a capture catheter. The guide wire should safely pass through the safe zone between the right atrium and the right ventricle. That is, when the safe zone catheter is positioned in the right ventricle through the safe zone, a guide wire is inserted through the hole in the safe zone catheter. The guide wire would be preferably inserted up to the pulmonary artery. When the guide wire is inserted up to the pulmonary artery, the safe zone catheter is taken out and a capture catheter that can capture a intervention wire in the right ventricle is inserted along the guide wire through the hole.

The term "capture catheter" means a catheter for capturing a intervention wire in the right ventricle and may be called a "wire guidance device" in tams that it guides a intervention wire to the inferior vena cava. Since a hole is formed in the capture catheter, the capture catheter is inserted into the right ventricle along the guide wire through the hole.

FIG. 14 is a view illustrating a process of capturing a intervention wire using a mesh of a capture catheter of the present invention.

The mesh is contracted before it is inserted into the right ventricle and is expanded in the right ventricle, and a intervention wire is put into the mesh and then captured by contracting the mesh. That is, the mesh is expanded or contracted by operation from the outside and should have a size such that a intervention wire can be easily passed though when it is expanded and a intervention wire can be held tight when it is contracted. When a intervention wire passes through the mesh, the mesh is contracted by an operation unit outside. Then, the intervention wire is captured in the mesh.

Referring to FIG. 14, (a) shows a state when a capture catheter is inserted in the right ventricle, (b) shows a state when a mesh that is a capture catheter is expanded in the right ventricle, and (c) shows a state when a intervention wire that has passed through an interventricular septum has passed through a mesh. (d) and (c) show the same state, (e) shows a state when the intervention wire has been captured by contracting the mesh, and (f) shows a state when the captured intervention wire is guided to the inferior vena cava by moving down the mesh to the inferior vena cava.

Figure 15:
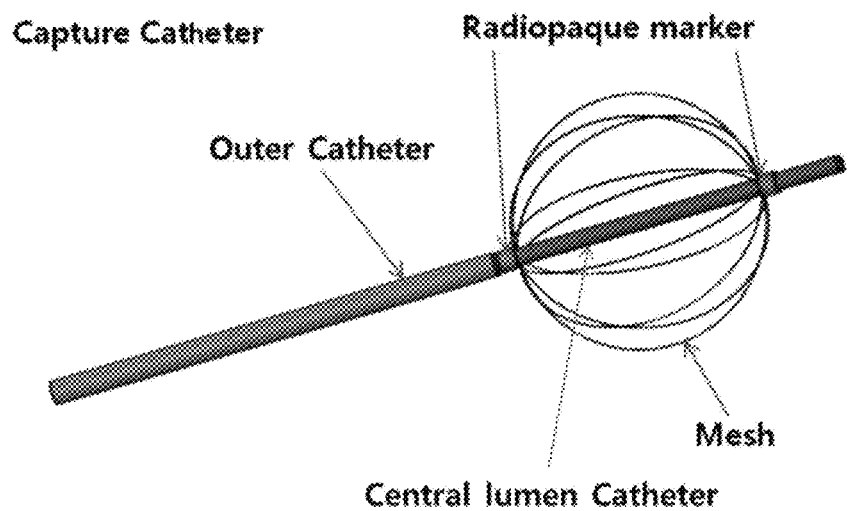
FIG. 15 is a view showing another example of a mesh that is disposed at an end of a capture catheter of the present invention.

It would be possible to check whether a intervention wire has passed through a mesh using existing displays. FIG. 15 is a view showing another example of a mesh that is disposed at an end of a capture catheter of the present invention. Preferably, as shown in FIG. 15, it would be possible to easily check it through a display by forming a radiopaque marker at the upper end or the lower end of a mesh.

The safe zone catheter and the capture catheter described above may be integrated in one surgical catheter. That is, a blocking member for passing through a safe zone may be formed at the front (upper) end and a capturing unit for capturing a intervention wire may be formed at the lower end.

Figure 16:
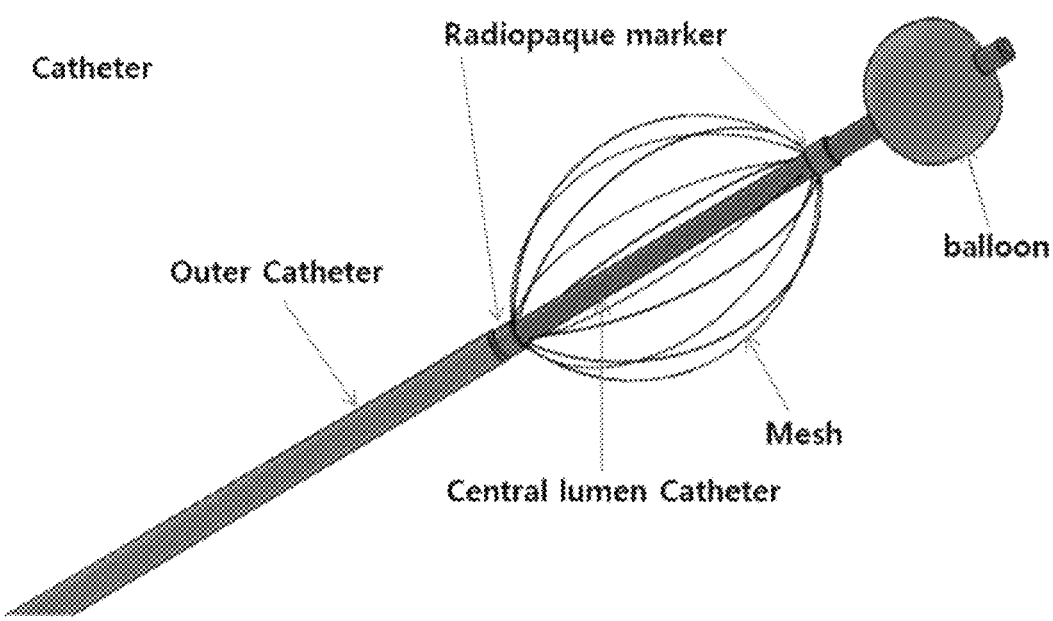
FIG. 16 is a view showing another example of a surgical catheter of the preset invention, in which a balloon is formed at the front (top) end and a mesh is formed under the balloon.

FIG. 16 is a view showing another example of a surgical catheter of the preset invention, in which a balloon is formed at the front (top) end and a mesh is formed under the balloon.

A blocking member for safe passing through a safe zone is formed at the upper end and a capturing unit (mesh) for capturing a intervention wire is formed at the lower end.

Though not shown, a safe zone catheter and a capture catheter may be inserted in one outer catheter. The integrated (safe zone+capture) catheter described above has a blocking member for passing through a safe zone at the front end and a capturing unit for capturing an intention wire at the lower end, but a separate safe zone catheter and a separate capture catheter may be inserted in one outer catheter.

Figure 17:
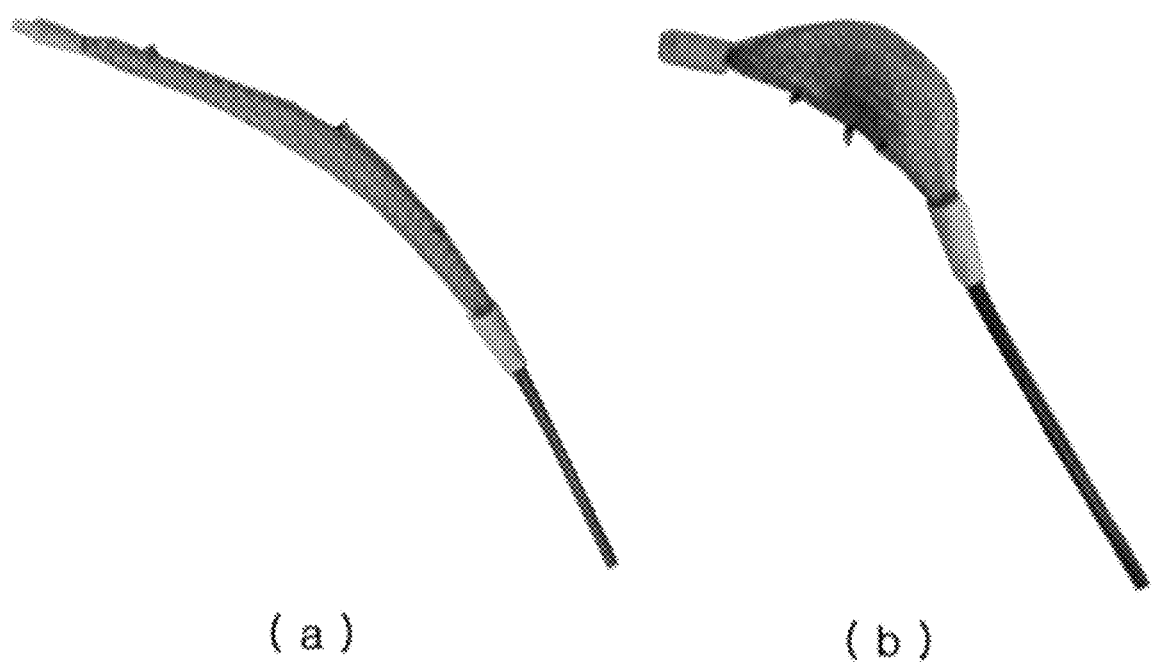
FIG. 17 is a picture showing a capture catheter having a D-shaped mesh as another example of a capture catheter of the present invention, in which (a) shows the state before the mesh expands and (b) shows the state after the mesh expands.

FIG. 17 is a picture showing a capture catheter having a D-shaped mesh as another example of a capture catheter for an operation of the present invention, in which (a) shows the state before the mesh expands and (b) shows the state after the mesh expands.

Referring to FIG. 17, the capture catheter is composed of an outer catheter, a central lumen catheter, and a mesh. In the mesh, the upper portion is closed and fixed to the central lumen catheter, and the lower portion is closed and fixed to the outer catheter.

A hole that a guide wire passes through is formed in the central lumen catheter. This is for guiding the capture catheter so that the capture catheter can be inserted into the right ventricle along a guide wire. The central lumen catheter can be inserted and moved up and down in the outer catheter.

In the capture catheter that is positioned in the right ventricle through a safe zone along a guide wire, when the outer catheter is pushed up by force from the outside of the body, the outer catheter will be moved up along the central lumen catheter and the mesh is expanded.

It is preferable that the mesh has a D-shaped structure when expanding. This will help when it is required to guide a wire particularly to the RVOT (right ventricular outflow tract) of the right ventricle, considering the structure of the right ventricle. That is, the D-shaped mesh expands wide toward the interventricular septum close to the RVOT, so a intervention wire can be more easily inserted through the mesh.

Referring to the figures, one or more connectors for coupling a first side of the mesh and the central lumen catheter to each other are formed so that the mesh has a D-shaped structure when expanding in the present invention. The connector is not fixed to the central lumen catheter, but moved up and down along the central lumen catheter, so when the mesh expands and contracts, the connector moves up and down along the central lumen catheter, whereby a second side of the mesh expands. The connector keeps holding the first side of the mesh, so when the mesh expands, the second side of the mesh expands wider, thereby making a D-shape.

Next, iii) the step (S30) of pulling out the intervention wire captured by the catheter toward the inferior vena cava by pulling out the catheter toward the inferior vena cava is performed.

When the capture catheter is pulled out toward the inferior vena cava with the intervention wire captured by the capture catheter, the intervention wire is also taken out toward the inferior vena cava. The capture catheter is fully pulled out of the body, whereby the intervention wire is also pulled out of the body.

Accordingly, in the intervention wire, one end is positioned outside over the body and the other end is positioned outside under the body through the superior vena cava, the coronary sinus, the interventricular septum, the right ventricle, the right atrium, and the inferior vena cava. Accordingly, the intervention wire generally makes an a-shaped loop.

Finally, iv) the step of positioning the tip of a lead in the interventricular septum by holding both ends of the intervention wire and inserting the lead of the pacemaker along the intervention wire is performed.

A hole (inner hole) is formed in the pacemaker lead so that a intervention wire can be inserted therein. The upper end and the lower end of the intervention wire protrude outside the body, so a surgeon holds both ends, passes the pacemaker lead through the inferior vena cava and the coronary sinus along the intervention wire through the hole, and then positions the lead in the interventricular septum.

The surgeon inserts the pacemaker lead while holding both ends of the intervention wire, thereby securing a sufficient support force that allows the tip of the pacemaker lead to be safely inserted into the interventricular septum tissues.

Preferably, the tip of the pacemaker lead is pointed to easily penetrate the interventricular septum tissues and has a blocking stop (a hook) not to be easily separated after being inserted in the interventricular septum tissues.

As described above, according to the present invention, since it is possible to directly and effectively apply electrical stimulus to the conduction system of the heart by positioning the tip of a pacemaker lead in the interventricular septum tissues, it is possible to obtain narrower QRS. Further, a intervention wire functions as a support, so it is possible to stably and simply insert the lead of a pacemaker into the interventricular septum tissues.

Embodiment

The inventor(s) performed a test of positioning the tip of a pacemaker lead in the interventricular septum using the heart of a pig. The pig used in the test was a female weighing about 50 kg.

The lead of the pacemaker was Boston scientific 4Fr ACUITY™ spiral Left ventricle (LV) lead.

The test was carried out in the same way as that described above.

Figure 18:
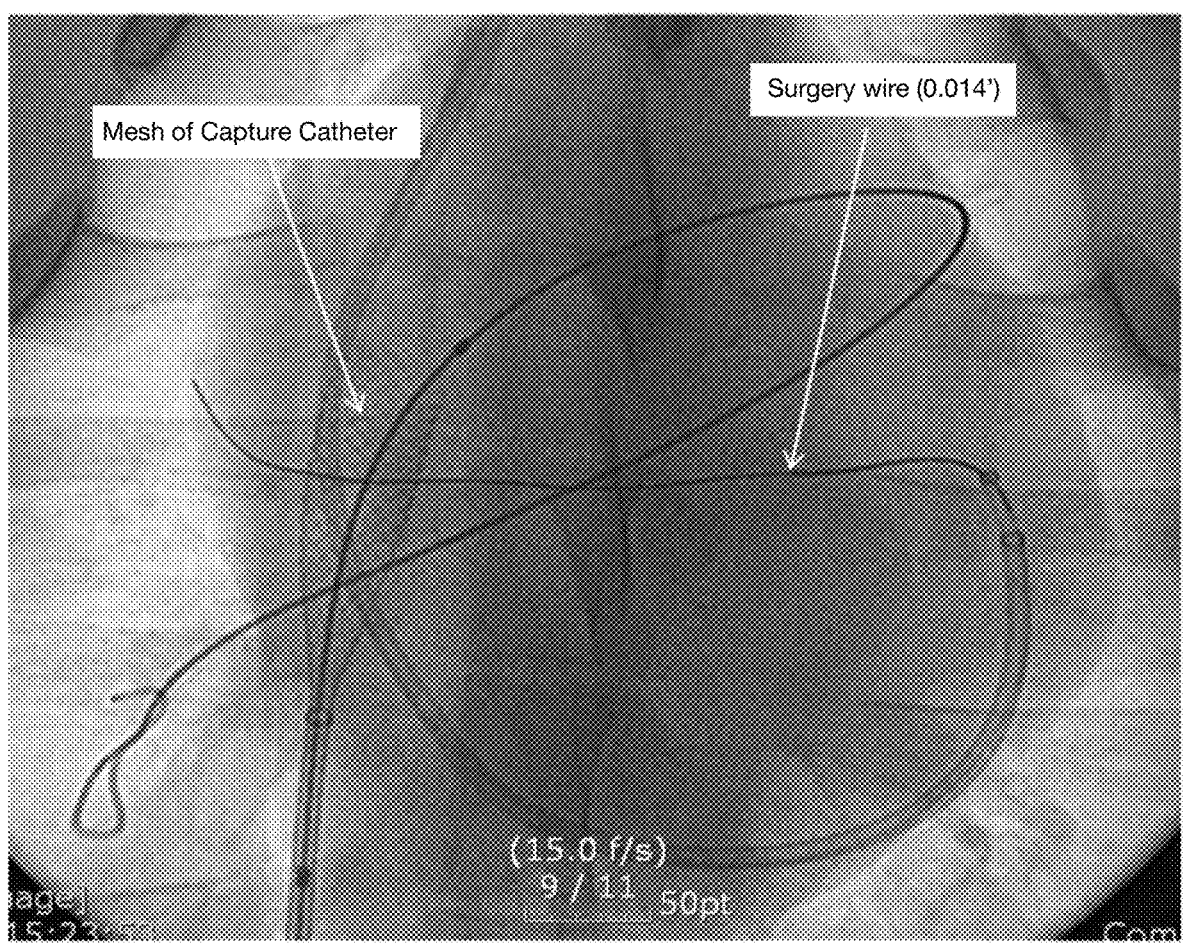
FIG. 18 is a picture when the mesh of a capture catheter captures a intervention wire passing through an interventricular septum in accordance with an embodiment of the present invention.

FIG. 5 is a picture of a pressurized septal venogram when a coronary sinus was blocked by a balloon catheter in the test and FIG. 18 is a picture when the mesh of a capture catheter captures a intervention wire passing through an interventricular septum in accordance with an embodiment of the present invention.

In order to compare Trans-coronary sinus intraseptal pacing of the present invention with the RVAP of the related art, the RVAP of the related art was performed after the test of the present invention was performed.

FIG. 19A is a picture showing a tip of a pacemaker lead inserted in tissues of an interventricular septum in accordance with an embodiment of the present invention and FIG. 19B is a picture showing a pacemaker lead according to Trans-coronary sinus intraseptal pacing of the present invention and a pacemaker lead positioned at an RV apex according to an RVAP of the related art.

Figure 20:
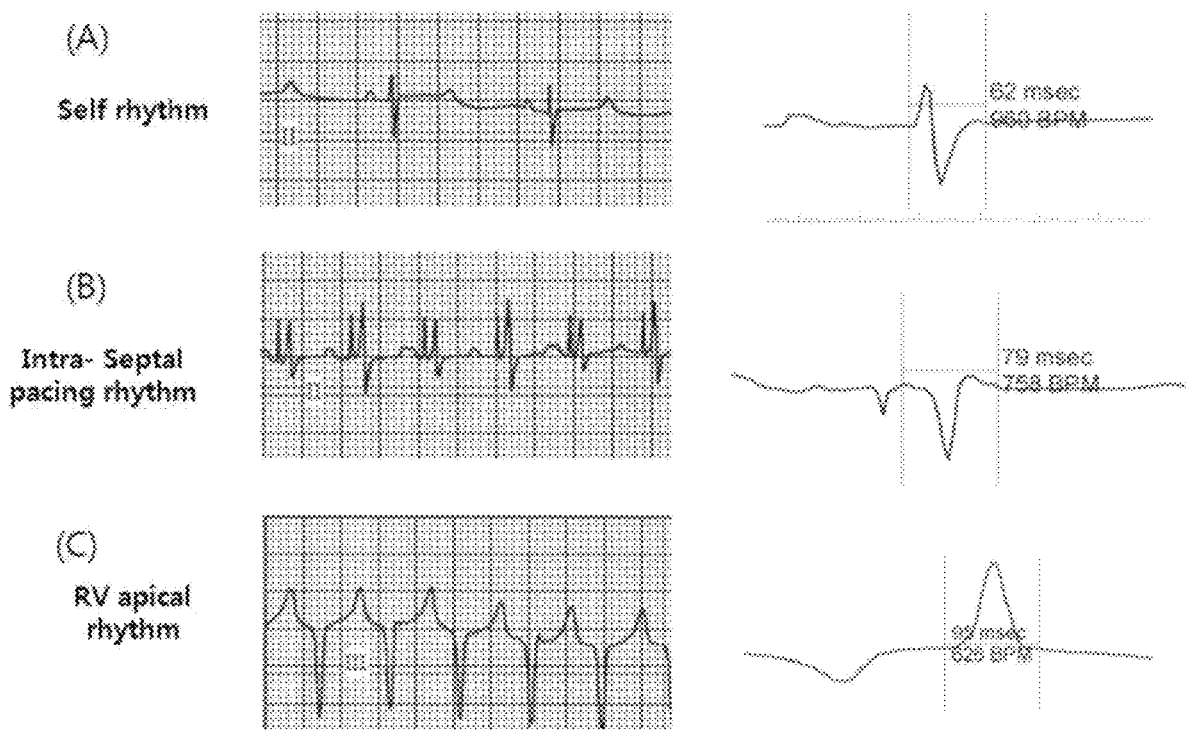
FIG. 20(A) shows natural QRS fluctuations in a pig used in a test.
FIG. 20(B) shows QRS fluctuation according to Intra-septal pacing according to the present invention.
FIG. 20(C) shows QRS fluctuations according to RVAP of the related art.

QRS intervals according to electrical stimulus positions in the test performed on a pig heart are shown in FIG. 20.

FIG. 20(A) shows natural QRS fluctuations in a pig used in the test, FIG. 20(B) shows QRS fluctuation according to Intra-septal pacing according to the present invention, and FIG. 20(C) shows QRS fluctuations according to RVAP of the related art.

The normal QRA (self-rhythm) of the pig's heart was 62 ms and the QRS (RV apical rhythm) in the RVAP of the related art was 95 ms, but the QRS in the Intra-septal pacing rhythm according to the present invention was 79 ms, so a considerably improved narrow QRS could be obtained.

Accordingly, the side effect causing a loss of ventricular function due to ventricular desynchronization was remarkably removed by overcoming a wide QRS that is a defect of the RVAP of the related art.

The above description is an example that explains the spirit of the present invention and may be changed and modified in various ways without departing from the basic features of the present invention by those skilled in the art. Accordingly, the embodiment described herein are provided not to limit, but to explain the spirit of the present invention and the spirit and the scope of the present invention are not limited by the embodiments. The protective range of the present disclosure should be construed on the basis of claims and all the technical spirits in the equivalent range should be construed as being included in the scope of the right of the present disclosure.

INDUSTRIAL APPLICABILITY

The present invention relates to a method, an apparatus, and a catheter for positioning a terminal end of a pacemaker lead that has passed through coronary sinus into an interventricular septum. Accordingly, the present invention can be applied to a method, an apparatus, and a catheter for positioning a terminal end of a pacemaker that has passed through a coronary sinus into an interventricular septum in order to more effectively transmit electrical stimulation in a treatment using a pacemaker for patients with arrhythmia.

The invention claimed is:

1. A method of positioning a distal portion of a pacemaker lead, the method comprising:
    a step of positioning an intervention wire through a proximal septal vein;

a step of inserting a safe zone catheter inserted in an inferior vena cava into a right ventricle through a right atrium and a safe zone of a tricuspid valve;

a step of inserting a guide wire through the safe zone catheter;

a step of pulling out the safe zone catheter toward the inferior vena cava with the guide wire maintained in the right ventricle of the heart;

a step of capturing the intervention wire with a capture catheter inserted along the guide wire;

a step of pulling out the intervention wire captured by the capture catheter toward the inferior vena cava by pulling out the capture catheter toward the inferior vena cava with the guide wire maintained in the right ventricle of the heart; and a step of holding both ends of the intervention wire and positioning the distal portion of the lead into an interventricular septum by inserting the pacemaker lead along the intervention wire.

2. The method of claim 1, wherein the step of positioning an intervention wire includes a step of finding the proximal septal vein positioned in the interventricular septum by inflating a balloon at a front end of a balloon-tipped guiding catheter to block and contrast a coronary sinus by injecting air into the balloon.

3. The method of claim 1, wherein the step of positioning an intervention wire includes a step of boring that uses an interventricular septum lumen catheter to bore the interventricular septum.

4. The method of claim 1, wherein the safe zone catheter further comprises a blocking member disposed on the distal end of the safe zone catheter.

5. The method of claim 4, wherein the blocking member of the safe zone catheter is in the shape of a balloon or a pig tail.

6. The method of claim 1, wherein the capture catheter comprises a mesh, and the method further comprises expanding or contracting the mesh.

7. The method of claim 1, wherein the capture catheter includes: a central lumen catheter having a hole therein for inserting a wire; an outer catheter moving up and down along the central lumen catheter; and a mesh having an upper portion closed and fixed to the central lumen catheter and a lower portion closed and fixed to the outer catheter.

8. The method of claim 1, wherein a hole for inserting the intervention wire is formed in the pacemaker lead and the distal portion of the pacemaker lead is pointed to easily penetrate the interventricular septum tissues.

9. A method of positioning a distal portion of a pacemaker lead, the method comprising:

a step of positioning an intervention wire into an interventricular septum through a proximal septal vein;

inserting a capture catheter inserted in an inferior vena cava into a right ventricle through a right atrium and a safe zone of a tricuspid valve and then capturing the intervention wire using a capturing unit of the capture catheter;

pulling out the capture catheter toward the inferior vena cava to pull out the intervention wire captured by the capture catheter toward the inferior vena cava; and positioning the distal portion of the lead into the interventricular septum along the intervention wire.

10. The method of claim 9, wherein the step of positioning an intervention wire includes a step of finding the proximal septal vein positioned in the interventricular septum by inflating a balloon at a front end of a balloon-tipped guiding catheter to block and contrast a coronary sinus by injecting air into the balloon.

11. The method of claim 9, wherein the step of positioning an intervention wire includes a step of boring that uses an interventricular septum lumen catheter to bore the interventricular septum.

12. The method of claim 9, wherein the capture catheter comprises a mesh, and the method further comprises expanding or contracting the mesh.

13. The method of claim 9, wherein the capture catheter includes: a central lumen catheter having a hole therein for inserting a wire; an outer catheter moving up and down along the central lumen catheter; and a mesh having an upper portion closed and fixed to the central lumen catheter and a lower portion closed and fixed to the outer catheter.

14. The method of claim 9, wherein a hole for inserting the intervention wire is formed in the pacemaker lead and the distal portion of the pacemaker lead is pointed to penetrate the interventricular septum.

15. A method of positioning a pacemaker lead comprising:

inserting an intervention wire into a coronary sinus, through a septal vein, and into an interventricular septum;

inserting the pacemaker lead along the intervention wire through the coronary sinus, through the coronary vein, and into the interventricular septum; and positioning the pacemaker lead inside the interventricular septum.

16. The method of claim 15, further comprising activating the pacemaker lead to apply electrical stimulation within the interventricular septum.

17. The method of claim 16, wherein the electrical stimulation by the pacemaker lead in the interventricular septum provides right ventricular pacing.

18. The method of claim 15, further comprising boring the intervention wire into the interventricular septum.

19. The method of claim 15, further comprising advancing the intervention wire out of the interventricular septum and into the right ventricle.

20. The method of claim 19, further comprising inserting a capture catheter into the right ventricle and grasping the intervention wire.

21. The method of claim 15, further comprising inserting a lumen catheter into the coronary sinus and into the septal vein;

advancing the intervention wire through the lumen catheter along the path taken by the lumen catheter;

deflecting the intervention wire at an angle away from inside the septal vein and towards the interventricular septum.

22. The method of claim 21, wherein the lumen catheter comprises a inclined ramp at its distal end to deflect the intervention wire at the angle.

23. The method of claim 21, further comprising performing a pressurized venogram of the sepal vein.

24. The method of claim 23, further comprising blocking the coronary sinus with a balloon while performing the pressurized venogram of the septal vein.

* * * * *